US012558352B2

(12) United States Patent
Wang et al.

(10) Patent No.: US 12,558,352 B2
(45) Date of Patent: Feb. 24, 2026

(54) USE OF MALIC ENZYME 1 (ME1) IN PREPARATION OF DRUG FOR PREVENTING AND TREATING PULMONARY HYPERTENSION (PH)

(71) Applicant: Institute of Basic Medical Sciences, CAMS, Beijing (CN)

(72) Inventors: Jing Wang, Beijing (CN); Yanjiang Xing, Beijing (CN); Ya Luo, Beijing (CN); Xianmei Qi, Beijing (CN)

(73) Assignee: Institute of Basic Medical Sciences, CAMS, Beijing (CN)

( * ) Notice: Subject to any disclaimer, the term of this patent is extended or adjusted under 35 U.S.C. 154(b) by 410 days.

(21) Appl. No.: 18/332,373

(22) Filed: Jun. 9, 2023

(65) Prior Publication Data

US 2024/0058330 A1 Feb. 22, 2024

(30) Foreign Application Priority Data

Jun. 21, 2022 (CN) ........................ 202210723098.8

(51) Int. Cl.
*A61K 31/496* (2006.01)
*A61P 9/12* (2006.01)

(52) U.S. Cl.
CPC .............. *A61K 31/496* (2013.01); *A61P 9/12* (2018.01)

(58) Field of Classification Search
CPC ......... A61K 31/496; A61K 45/00; A61P 9/12; A61P 9/04; C12Q 1/32; G01N 33/573; G01N 2333/902; G01N 2800/12; G01N 2800/321
USPC ..................................................... 514/254.01
See application file for complete search history.

(56) References Cited

PUBLICATIONS

Zhang et al Bioorganic & Medicinal Chemistry Letters, 2006, 16, 525-528 (Year: 2006).*

First Examination Report received in Chinese Application No. 202210723098.8, dated Feb. 18, 2023, 10 pages.

Li, Jin-Ian, et al., "Effects of nicotinamide on pulmonary arterial pressure and plasma endothelin in patients with cor pulmonale", Journal of Xinxiang Medical College, vol. 24, No. 5, Sep. 2007, pp. 441-442.

Ya, Luo, et al., "Malic Enzyme 1 and Its Research Progress on Disease Regulation", Advances in Physiological Sciences, vol. 52 Issue 3, 2021, pp. 181-186.

Zhang, Y. John, et al., "In silico design and synthesis of piperazine-1-pyrrolidine-2,5-dione scaffold-based novel malic enzyme inhibitors", Bioorganic & Medicinal Chemistry Letters, vol. 16, Issue 3, Feb. 1, 2006, pp. 525-528.

* cited by examiner

*Primary Examiner* — Yevgeny Valenrod
(74) *Attorney, Agent, or Firm* — CM Law PLLC; Robert C. Klinger

(57) ABSTRACT

The present disclosure belongs to the technical field of biomedicine, and specifically relates to use of a malic enzyme 1 (ME1) inhibitor in preparation of a drug for preventing and treating pulmonary hypertension (PH) and as a marker for detecting and/or treating the PH. Since a protein level and/or an enzymatic activity are significantly increased in a lung tissue, the ME1 can be used as a marker for detecting or treating the PH. Meanwhile, the ME1 inhibitor can ameliorate pulmonary vascular resistance (PVR) and right ventricular involvement/right heart failure in PH patients by reducing a right ventricular systolic pressure (RVSP) and a right ventricular hypertrophy index (RVHI). Therefore, the ME1 inhibitor can be used as a therapeutic target for treating the PH, thereby increasing a medical utility of the ME1 and the ME1 inhibitor.

4 Claims, 28 Drawing Sheets

Specification includes a Sequence Listing.

E

SEQUENCE LISTING

```
Sequence total quantity: 3
SEQ ID NO: 1            moltype = DNA  length = 25
FEATURE                 Location/Qualifiers
source                  1..25
                        mol_type = other DNA
                        note = sequence of forward primer 5'loxP-F
                        organism = synthetic construct
SEQUENCE: 1
aagataggcc caactcaact cgcac                                        25

SEQ ID NO: 2            moltype = DNA  length = 27
FEATURE                 Location/Qualifiers
source                  1..27
                        mol_type = other DNA
                        note = sequence of forward primer 3'loxP-F
```

-continued

```
                         organism = synthetic construct
SEQUENCE: 2
agaaaaatct taatgtcaaa gtaactg                                         27

SEQ ID NO: 3             moltype = DNA  length = 25
FEATURE                  Location/Qualifiers
source                   1..25
                         mol_type = other DNA
                         note = sequence of reverse primer 3'loxP-R
                         organism = synthetic construct
SEQUENCE: 3
cccaggttta agactgttca aatta                                           25
```

USE OF MALIC ENZYME 1 (ME1) IN PREPARATION OF DRUG FOR PREVENTING AND TREATING PULMONARY HYPERTENSION (PH)

CROSS REFERENCE TO RELATED APPLICATION

This patent application claims the benefit and priority of Chinese Patent Application No. 2022107230988, filed with the China National Intellectual Property Administration on Jun. 21, 2022, the disclosure of which is incorporated by reference herein in its entirety as part of the present application.

SEQUENCE LISTING

The instant application contains a Sequence Listing which has been submitted electronically in ASCII format and is hereby incorporated by reference in its entirety. Said ASCII copy, created on Jun. 6, 2023, is named GWP20230402512-sequencelisting.xml and is 4,197 bytes in size.

TECHNICAL FIELD

The present disclosure belongs to the technical field of biomedicine, and specifically relates to use of a malic enzyme 1 (ME1) in preparation of a drug for preventing and treating pulmonary hypertension (PH).

BACKGROUND

Pulmonary hypertension (PH) refers to a clinical pathophysiological syndrome caused by multiple etiologies and pathogenesis, and includes changes in pulmonary vascular structure and/or functions, progressive increase in pulmonary vascular resistance (PVR), and mean pulmonary arterial pressure (mPAP) of greater than or equal to 25 mmHg. If not being effectively controlled, PH can further develop into right heart failure and even death. The main pathological changes of PH include pulmonary vascular remodeling, distal pulmonary artery muscularization, vascular occlusion, and complex plexiform lesions. Such pulmonary vascular remodeling is considered to be critical for the onset and progression of PH. A mechanism involved in the pulmonary vascular remodeling mainly involves the following three classic pathways: endothelin pathway, nitric oxide pathway, and prostacyclin pathway. Targeted drugs for the above three pathways have achieved desirable therapeutic effects in clinical applications. However, these targeted drugs only improve the clinical symptoms of patients, but cannot effectively relieve or reverse the pulmonary vascular remodeling and the progression of PH. More and more studies have shown that metabolic reprogramming plays a key role in the pulmonary vascular remodeling and the progression of PH, and targeting key metabolic pathways/enzymes can ameliorate the progression of PH. Accordingly, starting from the metabolic reprogramming and the key metabolic enzymes is of great significance for finding new therapeutic targets of PH.

As a key enzyme in the tricarboxylic acid (TCA) cycle, malic enzyme (ME) can catalyze the oxidative decarboxylation of malic acid to form pyruvic acid, accompanied by the generation of NADPH. So far, three subtypes of ME have been identified in mammal cells, which are encoded by three homologous genes, respectively. According to their cellular distribution and coenzyme specificity, the three subtypes are named cytoplasmic NADP-dependent ME (ME1), mitochondrial NAD(P)-dependent ME (ME2), and mitochondrial NADP-dependent ME (ME3), respectively. These enzymes exist widely in nature, of which ME1 and ME2 are the main subtypes. ME1 is cytoplasmic and regulates pyruvic acid production, thus linking a glycolytic pathway with the TCA cycle. In addition, the ME1 can make a pathway of de novo fatty acid synthesis and glutamine metabolism interconnected by generating the NADPH. Studies have shown that ME1 is highly expressed in a variety of tumors. This enzyme leads to aerobic glycolysis by promoting glucose uptake and lactic acid accumulation, thereby enhancing proliferation and invasion of tumor cells. In hypertrophic heart disease, inhibition of ME1 is found to promote carbohydrate oxidation, reduce lactic acid accumulation, and increase glutathione content. In this way, an intracellular redox state is balanced to improve the functions of pathologically-hypertrophic heart. However, the role of ME in the occurrence and development of PH remains unknown.

SUMMARY

A purpose of the present disclosure is to provide use of an ME1 inhibitor in preparation of a drug for preventing and treating PH. ME1 can be used as a target for detecting and treating the PH. The ME1 inhibitor can be used as an active substance for preventing and treating the PH, thereby increasing use of the ME1 and the ME1 inhibitor.

The present disclosure provides use of an ME1 in preparation of a marker for detecting and/or treating PH.

Preferably, a protein level and/or an enzymatic activity of the ME1 is increased in a lung tissue.

The present disclosure further provides use of knock-out or knock-down of a gene encoding an ME1 in preparation of a drug for preventing and treating PH.

The present disclosure further provides use of an ME1 inhibitor in preparation of a drug for preventing and treating PH.

Preferably, the PH is induced by hypoxia and/or SU5416/hypoxia.

The present disclosure further provides use of an ME1 inhibitor in preparation of a drug for improving pulmonary vascular resistance (PVR) and/or pulmonary vascular remodeling.

The present disclosure further provides use of an ME1 inhibitor in preparation of a drug for one or more of reducing a right ventricular systolic pressure (RVSP), reducing a right ventricular hypertrophy index (RVHI), increasing a pulmonary artery acceleration time/ejection time (PA AT/ET), improving a tricuspid annular plane systolic excursion (TAPSE), and reducing a pulmonary artery medial thickness (PAMT).

Preferably, the ME1 inhibitor includes a small-molecule inhibitor ME1*.

The present disclosure further provides a drug for preventing and treating PH, where an active ingredient of the drug includes an ME1 inhibitor.

Preferably, the ME1 inhibitor includes a small-molecule inhibitor ME1*.

Beneficial Effects

The present disclosure provides use of an ME1 in preparation of a marker for detecting and/or treating PH. Since a protein level and/or an enzymatic activity are significantly increased in a lung tissue, the ME1 can be used as a marker for detecting or treating the PH.

Meanwhile, the present disclosure further provides use of an ME1 inhibitor in preparation of a drug for preventing and treating PH. The ME1 inhibitor can ameliorate PVR and right ventricular involvement/right heart failure in PH patients by reducing an RVSP and an RVHI. Therefore, the ME1 inhibitor can be used as a therapeutic target for treating the PH, thereby increasing a medical utility of the ME1 and the ME1 inhibitor.

BRIEF DESCRIPTION OF THE DRAWINGS

To describe the technical solutions in the examples of the present disclosure or in the prior art more clearly, the accompanying drawings required for the examples will be briefly described below.

FIG. 1A is a representative Western blot and relative quantitative analysis of ME in the lung tissues of PH patients (n=4) and healthy donors (n=4); FIG. 1B is representative immunohistochemical images and quantitative analysis of ME1 in the lung tissue sections of PH patients (n=4) and healthy donors (n=4); FIG. 1C is an enzymatic activity of ME1 in the lung tissues of PH patients (n=4) and healthy donors (n=4); the above data are expressed as median±interquartile range; a statistical method is Mann-Whitney U test; *P<0.05; n.s.: no significant difference; scale bar=50 μm;

FIG. 2A is a schematic diagram of the construction of chronic hypoxia-induced PH mouse model; FIG. 2B is a change of RVSP with an increase of hypoxia stimulation time; FIG. 2C is a change of a percentage (%) of RVHI with an increase of hypoxia stimulation time; FIG. 2D is a representative immunohistochemical image of α-SMA (red) in mouse lung tissue sections during chronic hypoxia-induced PH in mice; a change of a PAMT percentage includes pulmonary artery diameters of 0 μm to 50 μm and 50 μm to 100 μm; FIG. 2E is a schematic diagram of the construction of SuHx-induced PH mouse model; FIG. 2F is a change of RVSP with an increase of SuHx stimulation time; FIG. 2G is a change of RVHI (%) with an increase of SuHx stimulation time; FIG. 2H is a representative immunohistochemical image of α-SMA (red) in mouse lung tissue sections during SuHx-induced PH in mice; a change of a PAMT percentage includes pulmonary artery diameters of 0 μm to 50 μm and 50 μm to 100 μm; the above data are expressed as mean±standard error; n=8 mice per group; one-way analysis of variance; *P<0.05, P<0.01, *P<0.001 and ****P<0.0001; n.s.: no significant difference; scale bar=25 μm;

FIG. 3A is a representative Western blot and relative quantitative analysis of ME1 in mouse lung tissues exposed to chronic hypoxia; FIG. 3B is an enzymatic activity of the ME1 in mouse lung tissues exposed to chronic hypoxia; FIG. 3C is a representative Western blot and relative quantitative analysis of ME1 in mouse lung tissues exposed to SuHx; FIG. 3D is an enzymatic activity of the ME1 in mouse lung tissues exposed to SuHx; the above data are expressed as median±interquartile range; n=8 mice per group; a statistical method is one-way analysis of variance; *P<0.05, P<0.01, *P<0.001 and ****P<0.0001; n.s.: no significant difference;

FIG. 5A is a typical diagram of genotype identification of newborn wild-type (Me1+/+) mice and systemic knock-out (Me1−/−) mice; FIG. 5B is a representative Western blot of Me1 in the lung tissues of Me1+/+ and Me1−/− mice;

FIG. 6A is a schematic diagram of Me1+/+ and Me1−/− mouse PH induced by chronic hypoxia (Hx) or SuHx; FIG. 6B is a change of RVSP; FIG. 6C is a change of RVHI (%); FIG. 6D is representative echocardiogram and statistical diagram of PA AT/ET; FIG. 6E is representative echocardiogram and statistical diagram of TAPSE; FIG. 6F is a representative image of α-SMA immunohistochemistry of mouse lung tissue sections exposed to normoxia (Nor), Hx, or SuHx; a change of a PAMT percentage includes pulmonary artery diameters of 0 μm to 50 μm and 50 μm to 100 μm; all data are expressed as mean±standard error; n=8 mice in normoxia group, n=12 mice in Hx or SuHx group; two-way ANOVA; *P<0.001 and **P<0.0001 compared with normoxia-exposed Me1+/+ mice; ##P<0.01, ###P<0.001, and ####P<0.0001 compared with Me1−/− mice exposed to Hx or SuHx; scale bar=25 μm;

FIG. 7A is to evaluate the inhibition efficiency of ME1* (doses of 1 mg/kg, 10 mg/kg, 100 mg/kg, 200 mg/kg, and 500 mg/kg) on an enzymatic activity of ME1 in the lung tissues of normoxia mice; FIG. 7B is a schematic diagram of ME1* preventive treatment of SuHx-induced PH mice; the above data are expressed as mean±standard error; n=3 mice per group; one-way analysis of variance; **P<0.01; n.s.: not statistically significant;

FIG. 8A is a change of RVSP after ME1* or Vehicle preventive treatment of normoxia or SuHx mice; FIG. 8B is a change of RVHI (%) after ME1* or Vehicle preventive treatment of normoxia or SuHx mice; FIG. 8C is a representative immunohistochemical image of α-SMA (red) in lung tissue sections of mice exposed to normoxia or SuHx; a change of a PAMT percentage includes pulmonary artery diameters of 0 μm to 50 μm and 50 μm to 100 μm; FIG. 8D is representative echocardiogram and statistics of PA AT/ET in ME1* or Vehicle prophylactically treated normoxia or SuHx mice; FIG. 8E is representative echocardiogram and statistics of TAPSE in ME1* or Vehicle prophylactically treated normoxia or SuHx mice; all data are expressed as mean±standard error; n=6 mice in normoxia group, n=10 mice in SuHx group; two-way analysis of variance; P<0.01, *P<0.001, and ****P<0.0001 (compared with normoxia-exposed Vehicle group); #P<0.05, ##P<0.01, ###P<0.001, and ####P<0.0001 (compared with SuHx-exposed ME1* group); scale bar=25 μm; FIG. 9A is evaluation of an effect of ME1* on a body weight of mice after treatment; FIG. 9B is representative HE staining images of lung, heart, liver, spleen, kidney, and small intestine of the mice; the above data are expressed as mean values; n=6 mice in normoxia group and n=10 mice in SuHx group; one-way analysis of variance; scale bar=50 μm.

DETAILED DESCRIPTION OF THE EMBODIMENTS

Figure 1A:
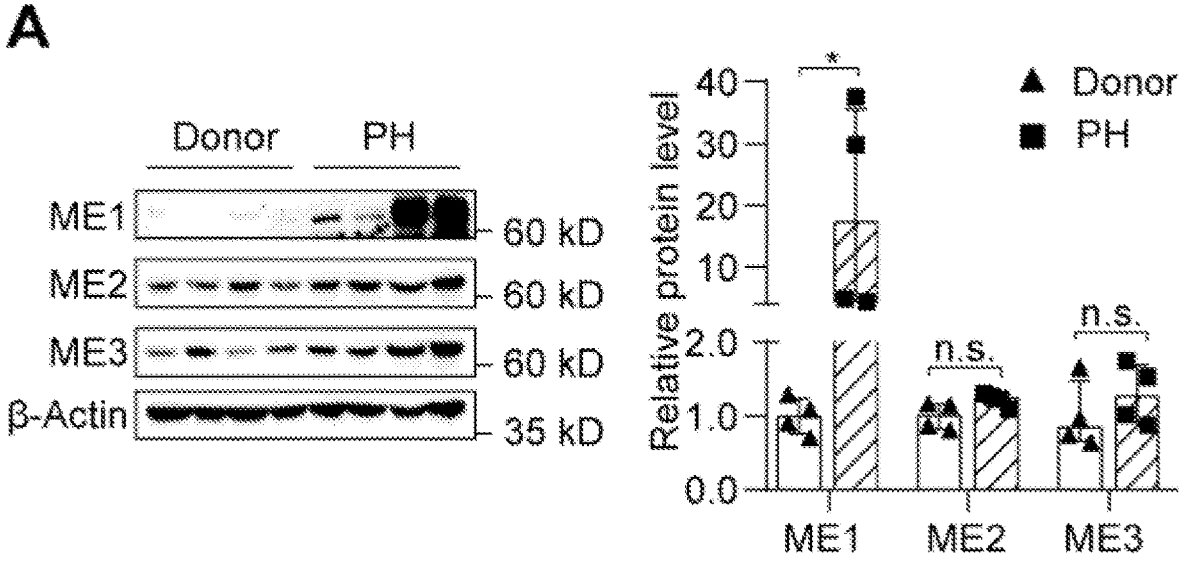
FIGS. 1A-C show that a protein level and an enzymatic activity of the ME1 are increased in lung tissues of PH patients, where

The present disclosure provides use of an ME1 in preparation of a marker for detecting and/or treating PH. In the present disclosure, the ME1 is highly expressed in the lung tissue samples of PH, and the protein level and enzymatic activity are increased. Therefore, the ME1 can be used as a marker for detecting PH and a target for treating PH.

The present disclosure further provides use of knock-out or knock-down of a gene encoding an ME1 in preparation of a drug for preventing and treating PH. The knock-out is preferably systemic knock-out. The drug includes preferably a diagnostic and therapeutic preparation. By knock-out of a coding gene Me1 of the ME1, the PVR and right ventricular involvement/right heart failure of PH patients or model animals can be significantly improved, thereby preventing and treating the PH.

The present disclosure further provides use of an ME1 inhibitor in preparation of a drug for preventing and treating PH. In the present disclosure, the following contents all belong to the protection scope of the present disclosure: use of an ME1 inhibitor in preparation of a drug for improving PVR and/or pulmonary vascular remodeling; use of an ME1 inhibitor in preparation of a drug for one or more of reducing an RVSP, reducing an RVHI, increasing a PA AT/ET, improving a TAPSE, and reducing a PAMT. The ME1 inhibitor includes preferably a small-molecule inhibitor ME1*; the small-molecule inhibitor ME1* has a chemical structure preferably shown in Formula I, and has a CAS number of 522649-59-8. The drug includes preferably a diagnostic and therapeutic preparation.

Formula I

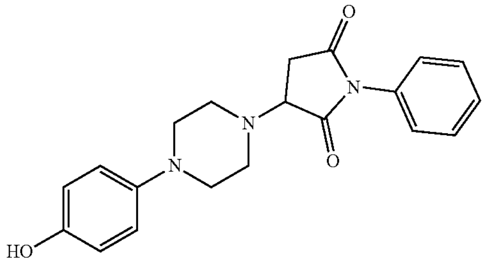

In the present disclosure, the pH includes preferably hypoxia-induced pH and SU5416/hypoxia (SU5416 combined with hypoxia)-induced pH. The ME1 inhibitor can effectively reduce RVSP and RVHI, increase PA AT/ET and TAPSE, reduce PAMT, thus ameliorating PVR, right ventricular involvement and/or right heart failure. In this way, pulmonary vascular remodeling and delaying PH are achieved. The ME1 inhibitor can be used to prepare a drug for treating PH.

The present disclosure further provides a drug for preventing and treating PH, where an active ingredient of the drug includes an ME1 inhibitor. The ME1 inhibitor includes preferably a small-molecule inhibitor ME1*. The drug further includes preferably pharmaceutically acceptable auxiliary materials. There is no special limitation on the auxiliary materials, and conventional auxiliary materials in the art can be used. The drug is preferably injected intraperitoneally.

In order to further illustrate the present disclosure, the technical solutions provided by the present disclosure will be described in detail below in conjunction with accompanying drawings and examples, but they should not be construed as limiting the protection scope of the present disclosure.

Example 1

ME1 was Highly Expressed in the Lung Tissues of PH Patients and PH Mice 1.1 Collection of Human Lung Tissue Samples The lung tissue (n=4) of an experimental group came from a patient with advanced PH receiving lung transplantation; the lung tissue in a control group (n=4) was obtained from parts of healthy donors resected due to lung size mismatch during lung transplantation. Informed consent was obtained from all participants for this study. The human lung tissue used had been approved by the Ethics Committee of Peking Union Medical College (approval number: 2018043) and Fuwai Hospital (approval number: 2017-877).

1.2 Collection of Lung Tissues from C57BL/6J Mice Exposed to Simple Hypoxia for 0, 1, 2, 3, and 4 Weeks 8 to 10 week-old SPF-grade C57BL/6J male mice weighing 25 g to 30 g were fed in a hypoxia chamber (an oxygen concentration in the chamber was maintained at 10%) for 0 weeks (n=8), 1 week (n=8), 2 weeks (n=8), 3 weeks (n=8), and 4 weeks (n=8). The mouse lung tissues were collected and assessed for RVSP and RVHI and analyzed for PAMT.

1.3 Collection of Lung Tissues from C57BL/6J Mice Exposed to SuHx for 0, 1, 2, and 3 Weeks 8 to 10 week-old SPF-grade C57BL/6J male mice weighing 25 g to 30 g were fed in a hypoxia chamber (an oxygen concentration in the chamber was maintained at 10%) while receiving weekly subcutaneous injections of 20 mg/kg of SU5416 for 0 weeks (n=8), 1 week (n=8), 2 weeks (n=8), and 3 weeks (n=8). The mouse lung tissues were collected and assessed for RVSP and RVHI and analyzed for PAMT.

1.4 Determination of RVSP and RVHI

The RVSP can be used to evaluate a pulmonary artery pressure (PAP) of the mouse, and the RVHI can reflect the right ventricular involvement and right ventricular hypertrophy of the mouse due to excessive PVR. The specific operation steps were as follows: (1) After anesthetized with 2% pentobarbital sodium (50 mg/kg by intraperitoneal injection), the mice were fixed on an operating board. (2) Power Lab was started and then connected to a pressure transducer. (3) The skin of the anterior chest wall of the mouse was cut with surgical scissors to clearly expose the position of manubrium sternum. (4) A 22-gauge needle was inserted into the right ventricle (RV) at 45° along an intersection point of the manubrium sternum and the left costal margin through the closed chest, and a position of the needle tip in the heart cavity was determined by the waveform; a stable RVSP waveform was saved and an RVSP measured value were recorded through Chart program. (5) The mice were sacrificed to obtain the heart; excess connective tissue and appendages in the heart were removed, and a free wall of the right ventricle was cut; the right ventricle, left ventricle, and interventricular septum (Left ventricular+septum, LV+S) were weighed to calculate RVHI=RV/LV+S.

1.5 Evaluation of PAMT

PAMT is used to analyze the morphological changes of pulmonary vessels. In the present disclosure, a primary antibody of α-smooth muscle actin (α-SMA), a surface marker of pulmonary vascular smooth muscle cells, was stained by immunohistochemistry, and then a percentage of PAMT was calculated to evaluate the pulmonary vascular remodeling of PH mice. A left lung tissue was collected and fixated in 10% neutral formalin at room temperature for at least 24 h; after being dehydrated by an automatic tissue dehydrator, the lung tissue was embedded in paraffin using a paraffin embedding-cold and hot platform integrated machine, and an obtained paraffin section of the lung tissue had a thickness of (4-5) μm. After deparaffinized and antigen retrieval (a pH of citric acid buffer was 6.0), the section was incubated with a primary antibody against α-SMA at 4° C. overnight, and then incubated with a horseradish peroxidase-bound secondary antibody. After counterstained with hematoxylin, cell nuclei were rinsed with tap water and differentiated with 0.5% hydrogen ethanol, soaked in tap water for 15 min, routinely dehydrated, subjected to transparent treatment, sealed with glycerogelatin and photographed. Statistical analysis: pulmonary vessel thickness was measured with a diameter of (0-50) μm and (50-100) μm. At least 20 vessels with a diameter of (0-50) μm and at least 15 vessels with a diameter of (50-100) μm were assessed per mouse, and the PAMT percentage was calculated as: (outer circumference/2π-inner circumference/2π)/(outer circumference/2π)×100.

1.6 Detection of ME Protein Level (1) After adding a tissue lysate containing RIPA and phosphatase inhibitor, the lung tissue was shredded thoroughly, completely homogenized until transparent, lysed on ice for 30 min, and then centrifuged at 13,000 rpm for 15 min at 4° C., and an obtained supernatant was total protein. (2) A protein concentration was determined by BCA method. (3) Protein cooking: the protein was treated in a 100° C. metal bath for 5 min. (4) Gel preparation, electrophoresis (20 μg protein per well) and membrane transfer were conducted. (5) After the membrane transfer, the protein was blocked with 5% special skim milk at room temperature for 1 h, and then washed briefly with 1×TBST. (6) After incubation on a primary antibody overnight at 4° C., the primary antibody was recovered and then washed 3 times with 1×TBST, (5-10) min each time. (7) After incubation on a secondary antibody at room temperature for 1 h, the secondary antibody was recovered and washed 3 times with 1×TBST, (5-10) min each time. (8) A Tanon automatic chemiluminescence/fluorescence image analysis system was used to collect protein signals, and a gray value of WB bands was analyzed by Image-Pro Plus software to calculate a relative level of the target protein.

1.7 Detection of ME Enzymatic Activity

Histone supernatants or mitochondrial extracts were used to detect ME1 enzymatic activity. (1) Liquid preparation: an ME1 reaction buffer (pH=7.4) was prepared from 67 mM triethanolamine and 5.0 mM manganese chloride. (2) Sample preparation: a protein lysate was centrifuged at 13,000 rpm for 15 min at 4° C. (3) Adding samples: a reaction system included ME1 reaction buffer+L-malic acid (3.3 mM)+β-$NADP^+$ (0.3 mM)+protein lysate, with a total volume of 150 μL. (4) Reading was done with a multi-functional microplate reader, at a reading temperature maintained at 37° C., and an absorbance value was monitored at a wavelength of 340 nm every 50 s for a total of 30 min. (5) The protein concentration was determined for standardization. (6) The change of absorbance per mg of protein per unit time was calculated.

1.8 Result Analysis

Figure 1B:
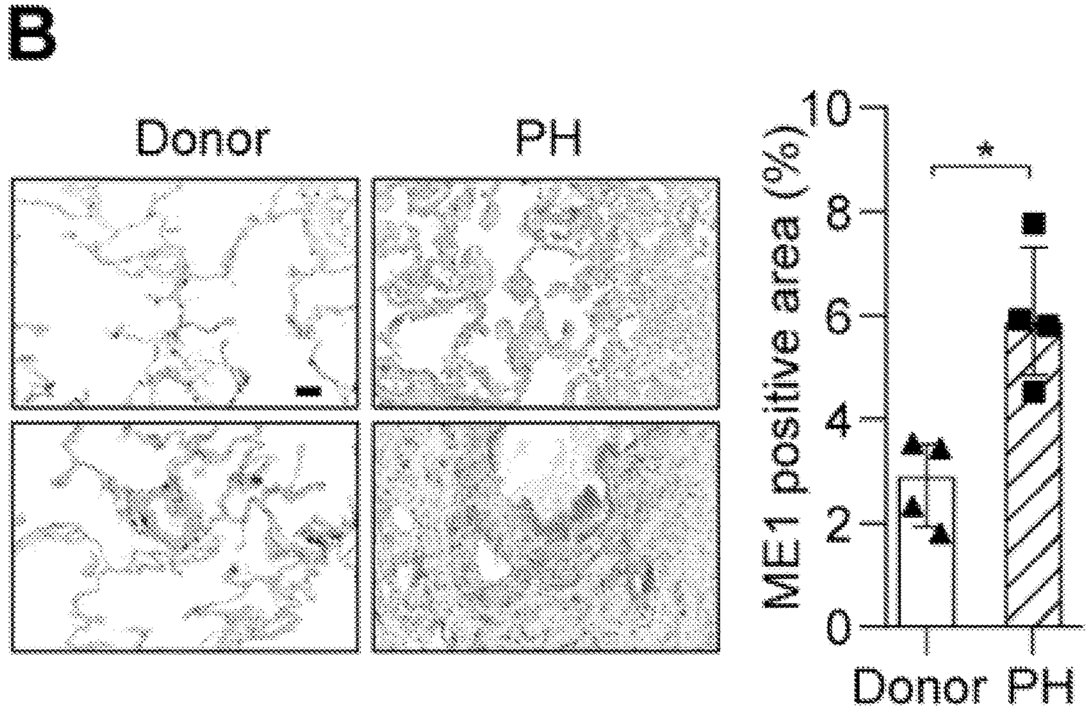
Figure 1C:
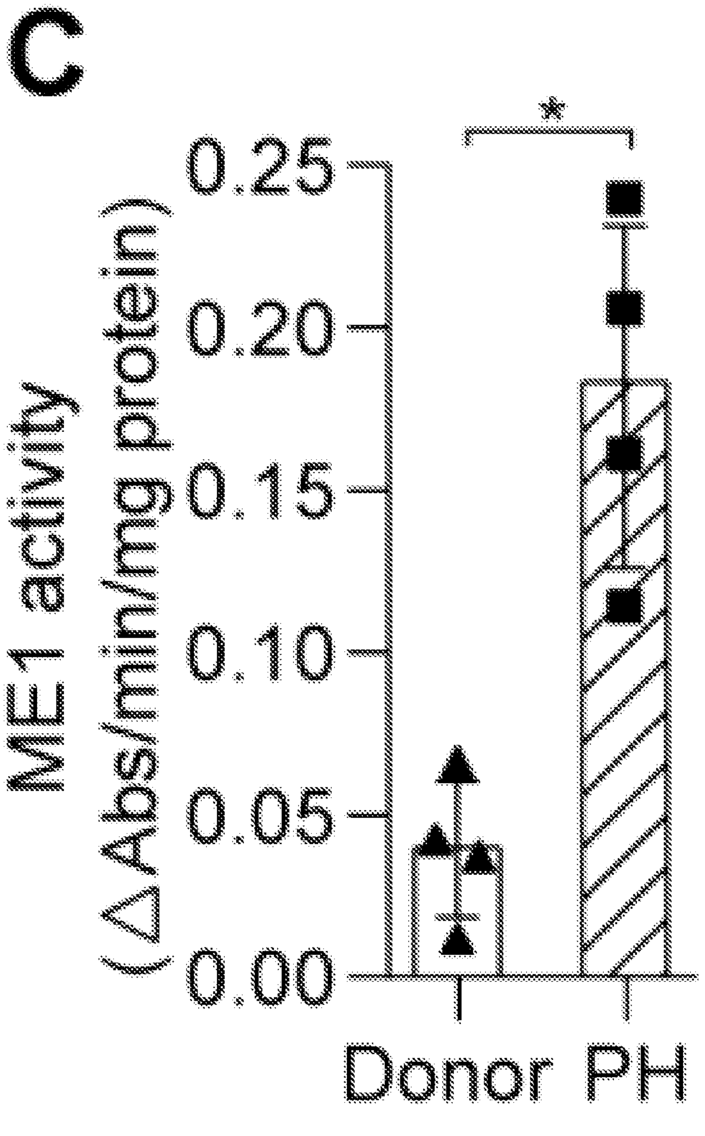

In the present disclosure, using malic enzyme 2 (ME2) and malic enzyme 3 (ME3) as controls, it was found that only the protein level and enzymatic activity of ME1 in the lung tissue of PH patients increased significantly, as shown in FIGS. 1A-C: where FIG. 1A was a representative Western blot and relative quantitative analysis of ME in the lung tissues of PH patients (n=4) and healthy donors (n=4); FIG. 1B was representative immunohistochemical images and quantitative analysis of ME1 in the lung tissue sections of PH patients (n=4) and healthy donors (n=4); FIG. 1C was an enzymatic activity of ME1 in the lung tissues of PH patients (n=4) and healthy donors (n=4). The above data were expressed as median±interquartile range; a statistical method was Mann-Whitney U test; *P<0.05; n.s.: no significant difference; scale bar=50 μm.

Figure 2A:
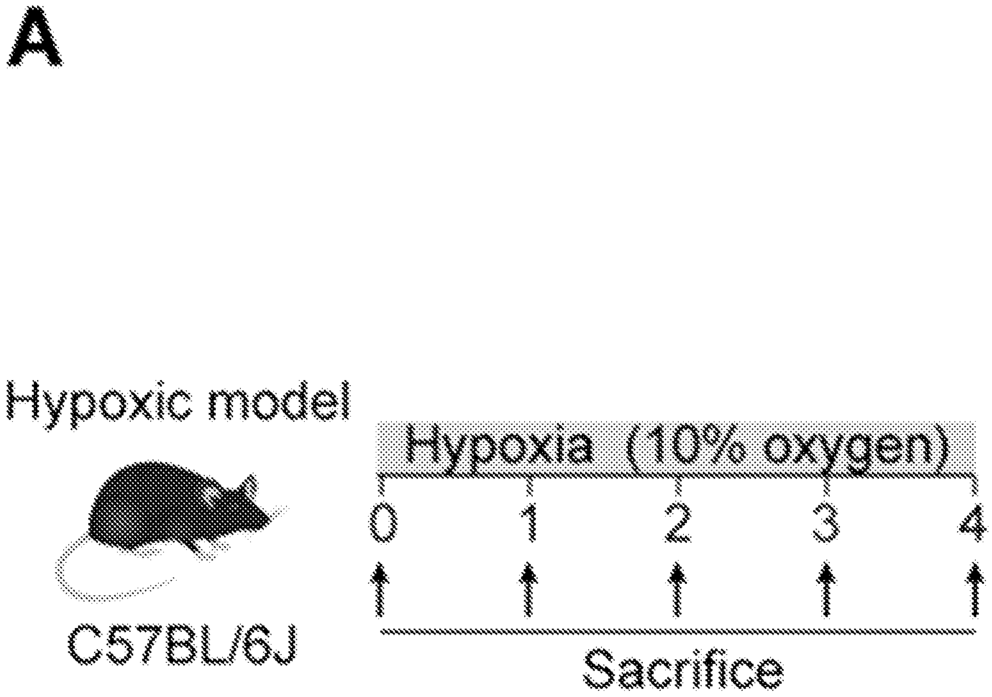
FIGS. 2A-H show construction and evaluation of chronic hypoxia- and SU5416/hypoxia (SuHx)-induced PH mouse models, where
Figure 2B:
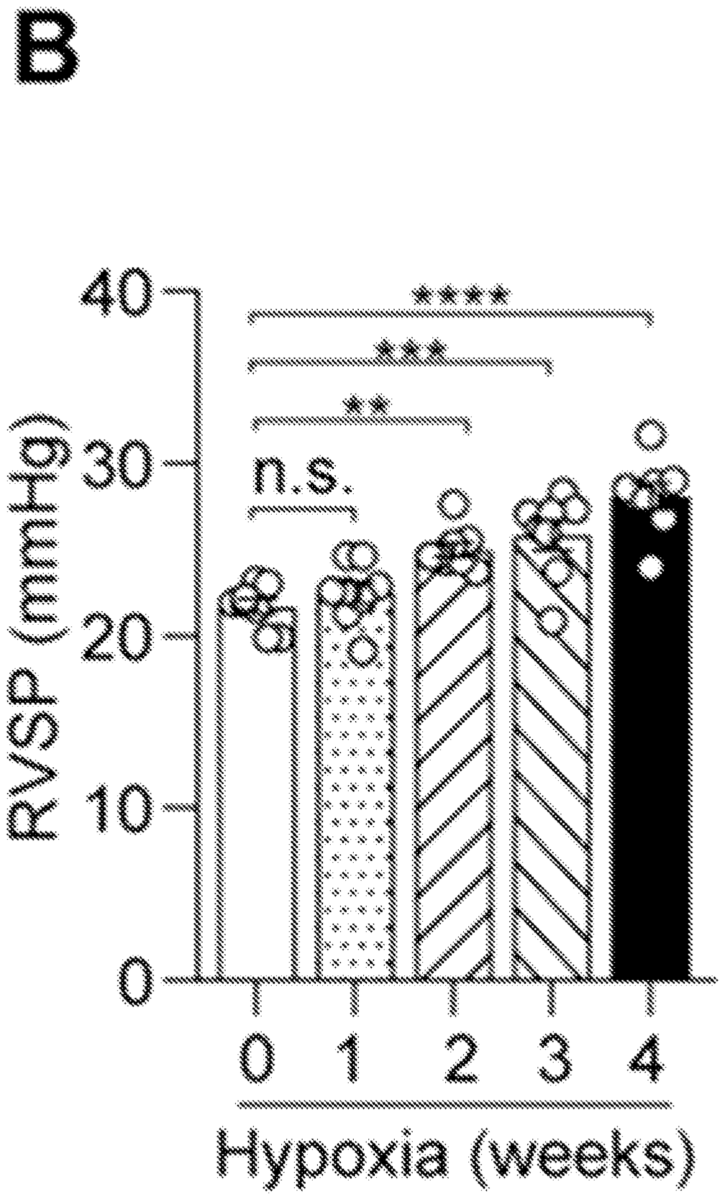
Figure 2C:
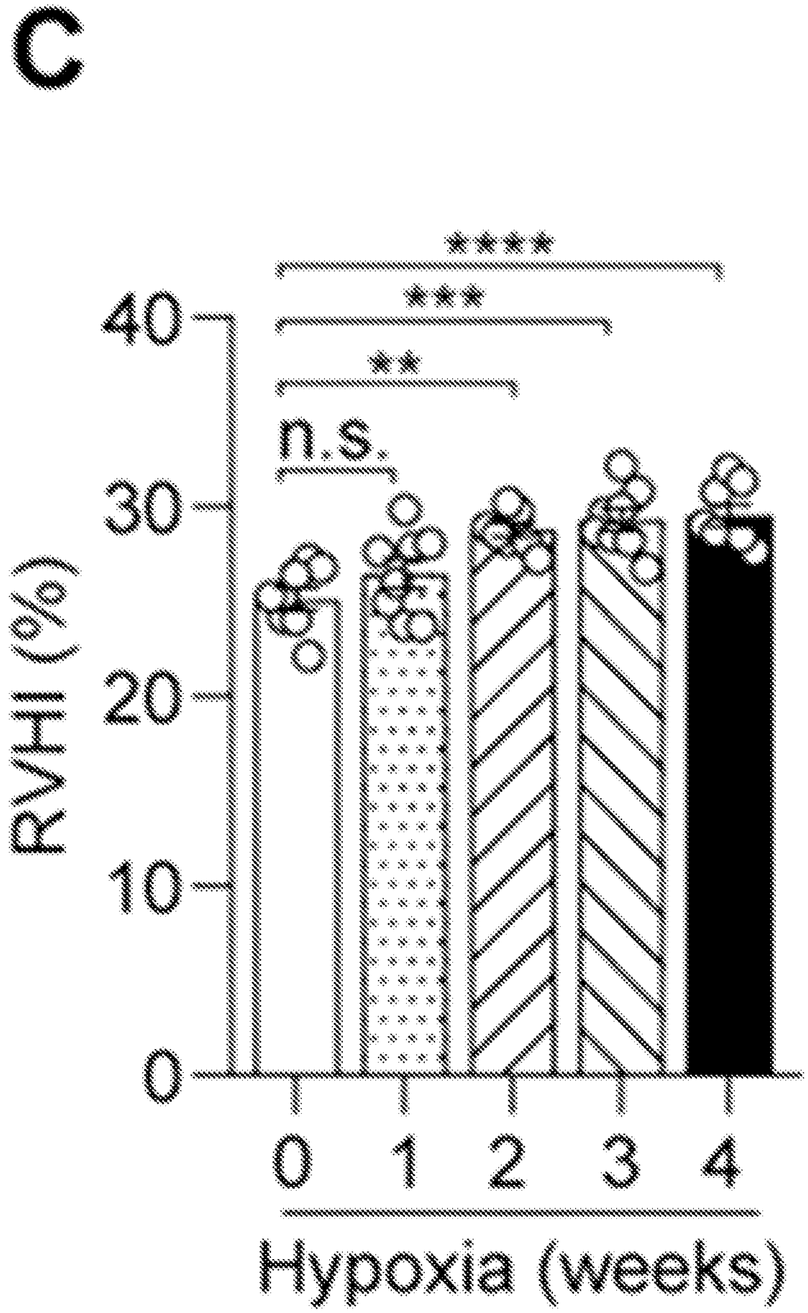
Figure 2D:
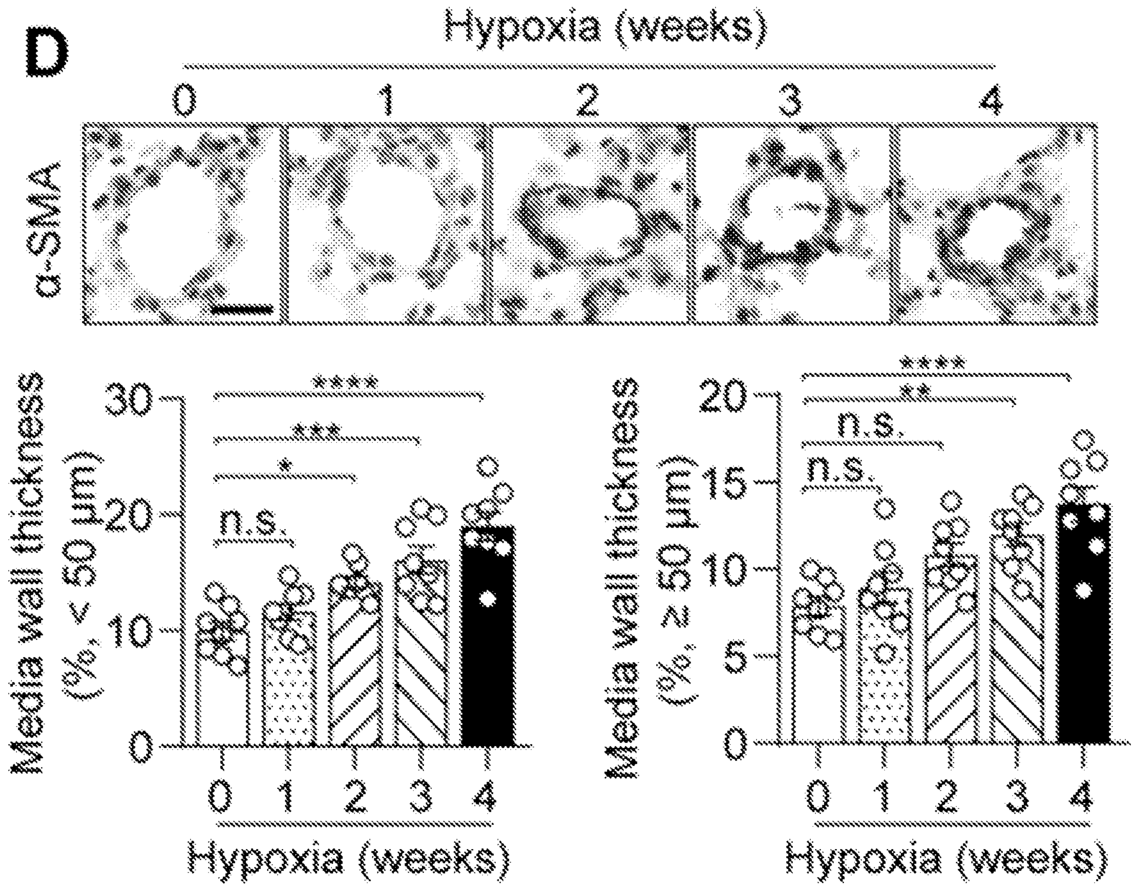
Figure 2E:
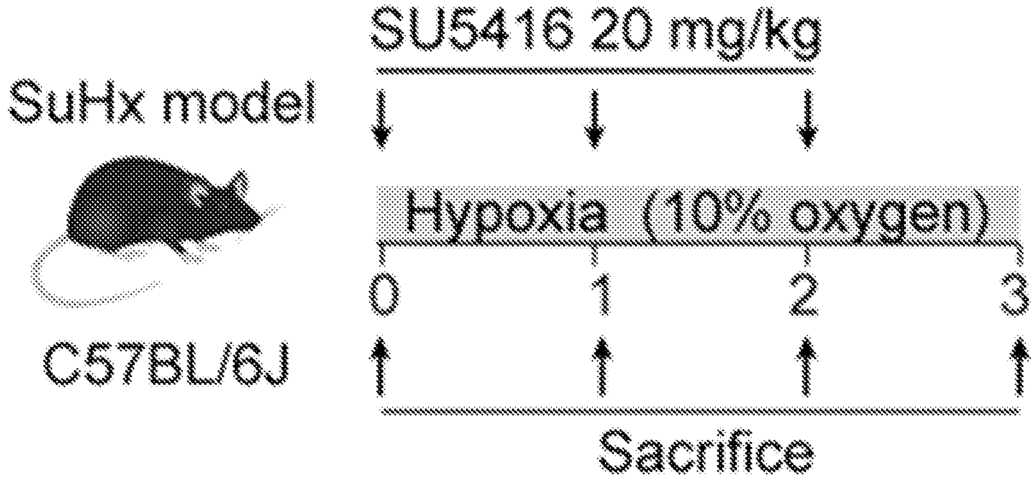
Figure 2F:
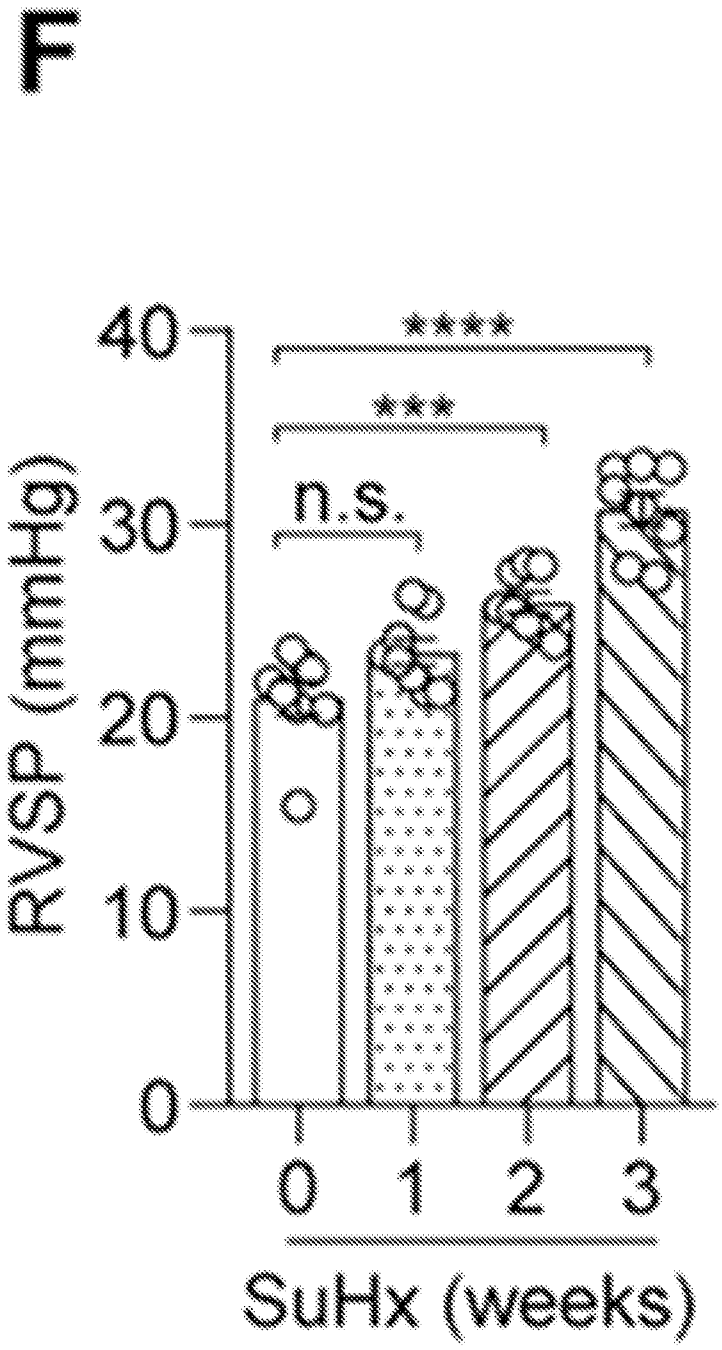
Figure 2G:
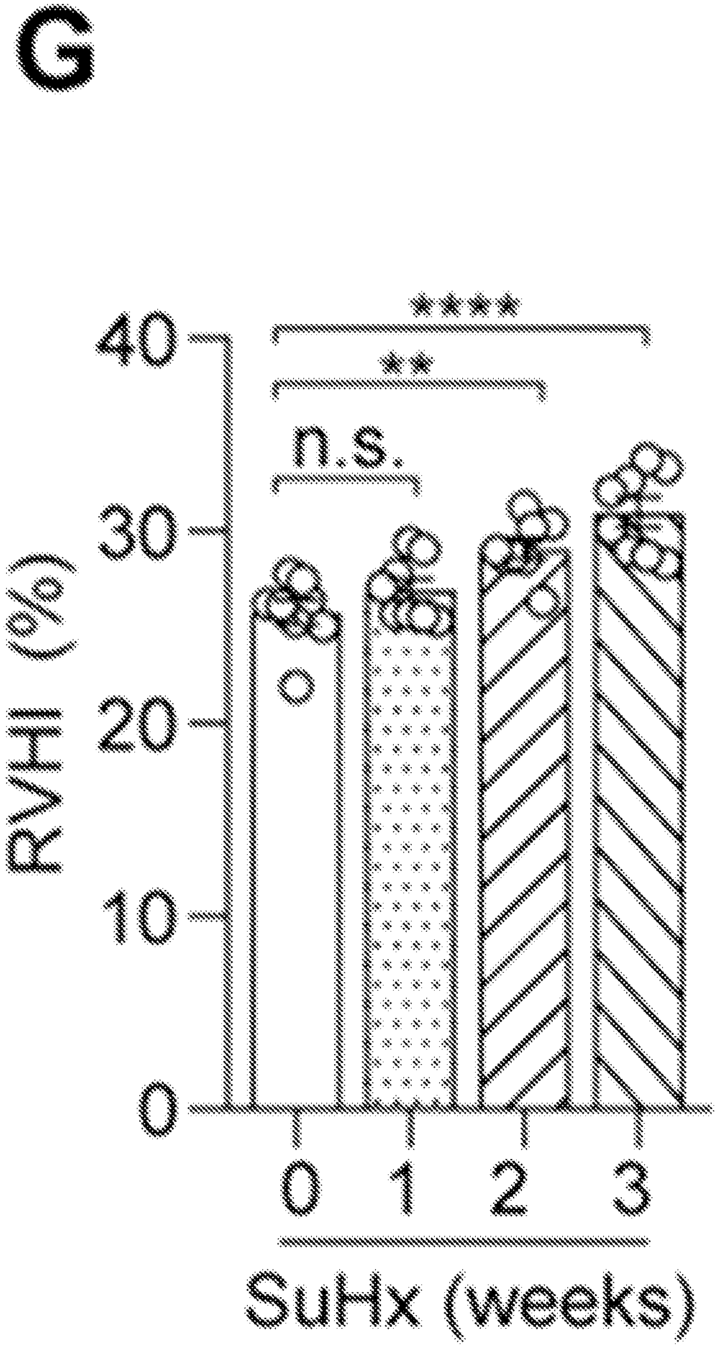
Figure 2H:
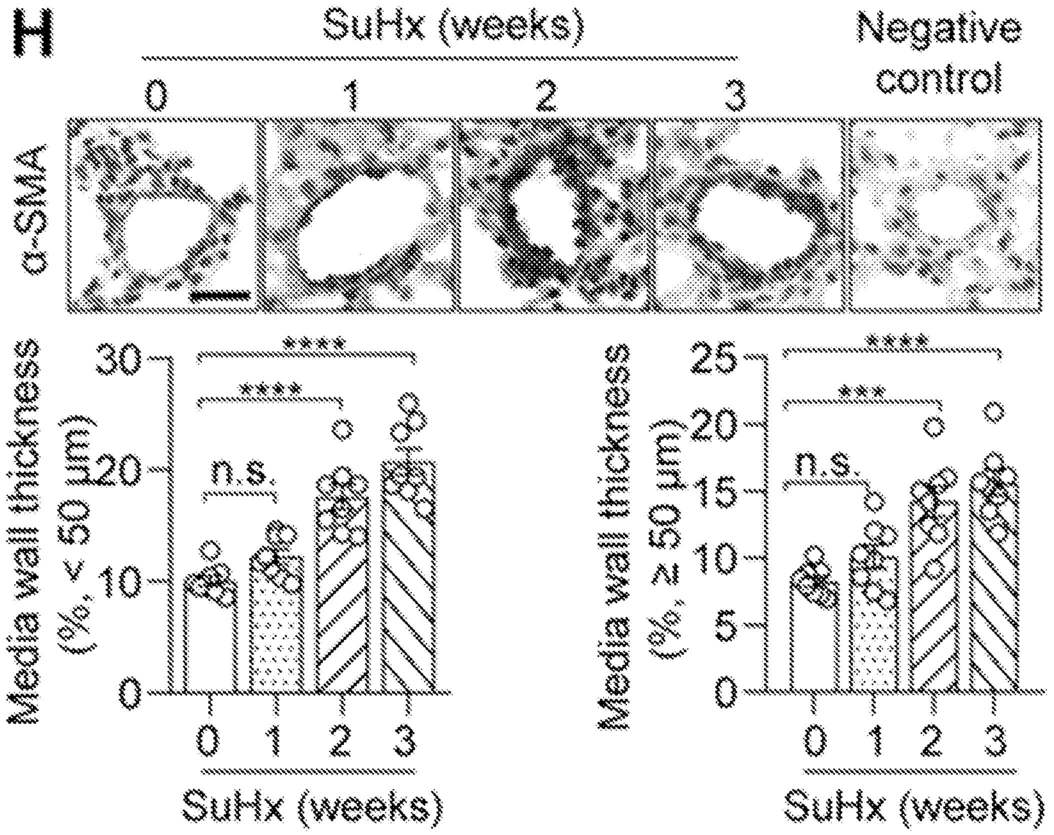

Further, chronic hypoxia-induced and SuHx-induced PH mouse models were constructed, as shown in FIGS. 2A-H: where FIG. 2A was a schematic diagram of the construction of chronic hypoxia-induced PH mouse model; FIG. 2B was a change of RVSP with an increase of hypoxia stimulation time; FIG. 2C was a change of a percentage (%) of RVHI with an increase of hypoxia stimulation time; FIG. 2D was a representative immunohistochemical image of α-SMA (red) in mouse lung tissue sections during chronic hypoxia-induced PH in mice; a change of a PAMT percentage included pulmonary artery diameters of 0 μm to 50 μm and 50 μm to 100 μm; FIG. 2E was a schematic diagram of the construction of SuHx-induced PH mouse model; FIG. 2F was a change of RVSP with an increase of SuHx stimulation time; FIG. 2G was a change of RVHI (%) with an increase of SuHx stimulation time; FIG. 2H was a representative immunohistochemical image of α-SMA (red) in mouse lung tissue sections during SuHx-induced PH in mice; a change of a PAMT percentage included pulmonary artery diameters of 0 μm to 50 μm and 50 μm to 100 μm. The above data were expressed as mean±standard error; n=8 mice per group; one-way analysis of variance; *P<0.05, P<0.01, *P<0.001 and ****P<0.0001; n.s.: no significant difference; scale bar=25 μm.

Figure 3A:
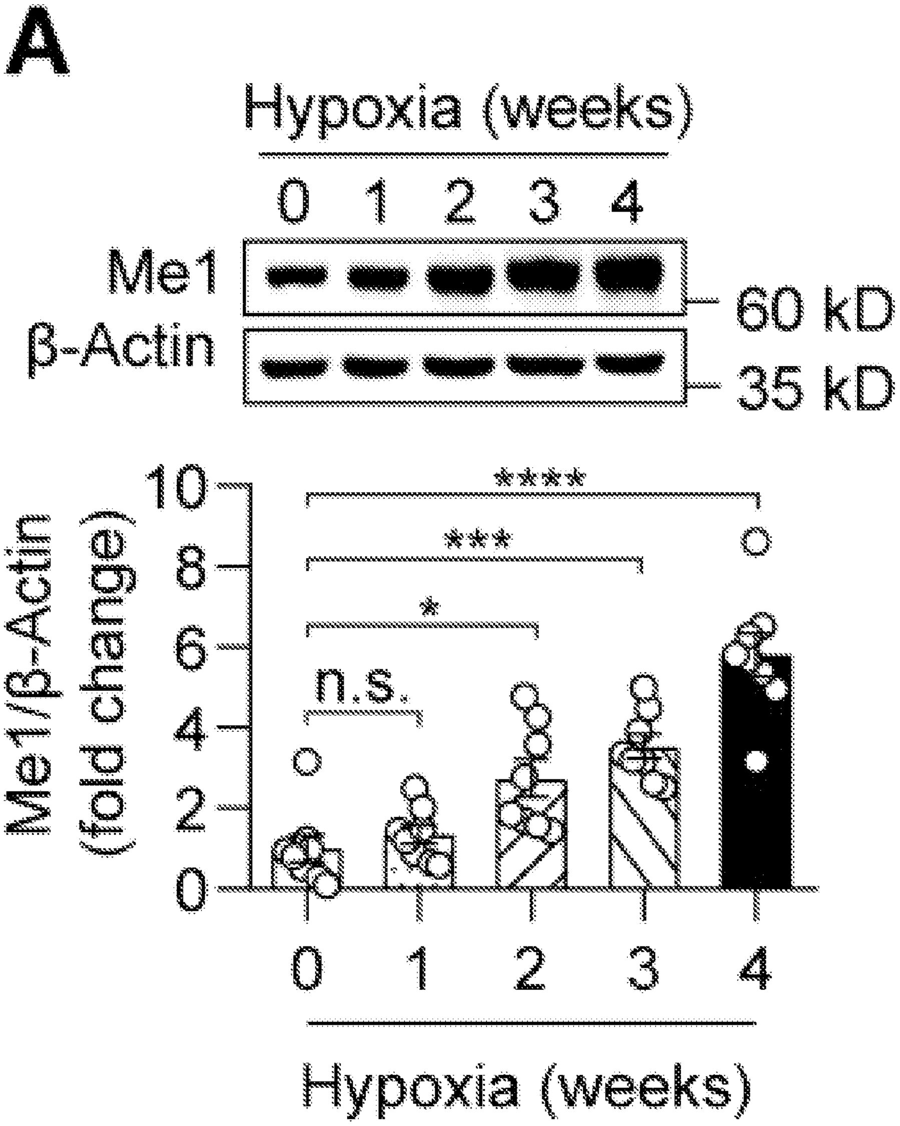
FIGS. 3A-D show that a protein level and an enzymatic activity of the ME1 are increased in lung tissues of PH mice, where
Figure 3B:
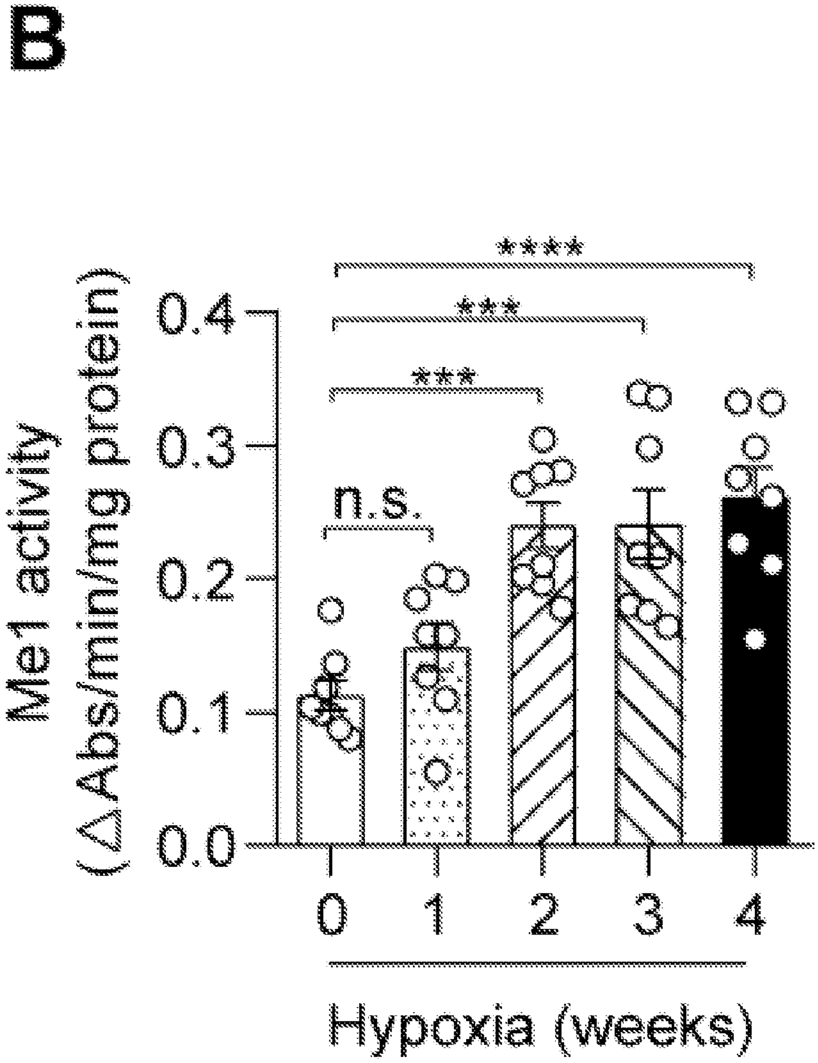
Figure 3C:
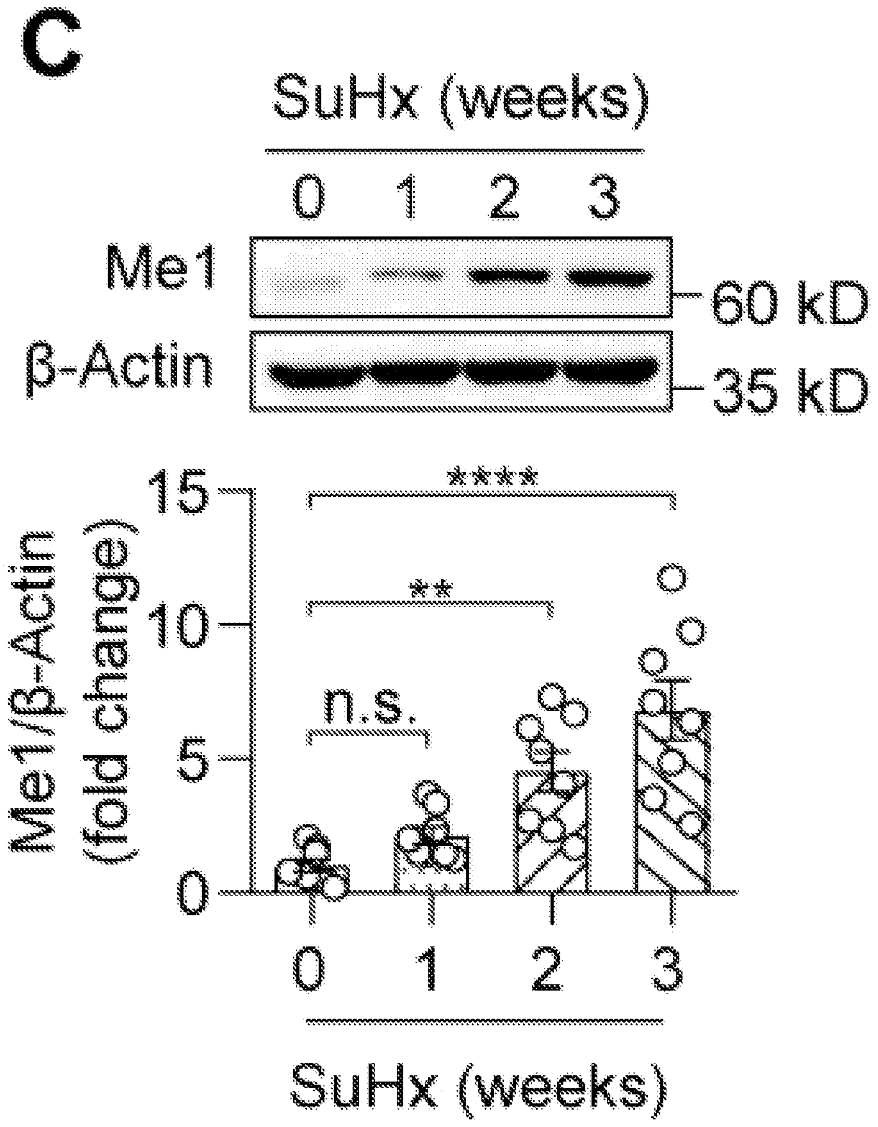
Figure 3D:
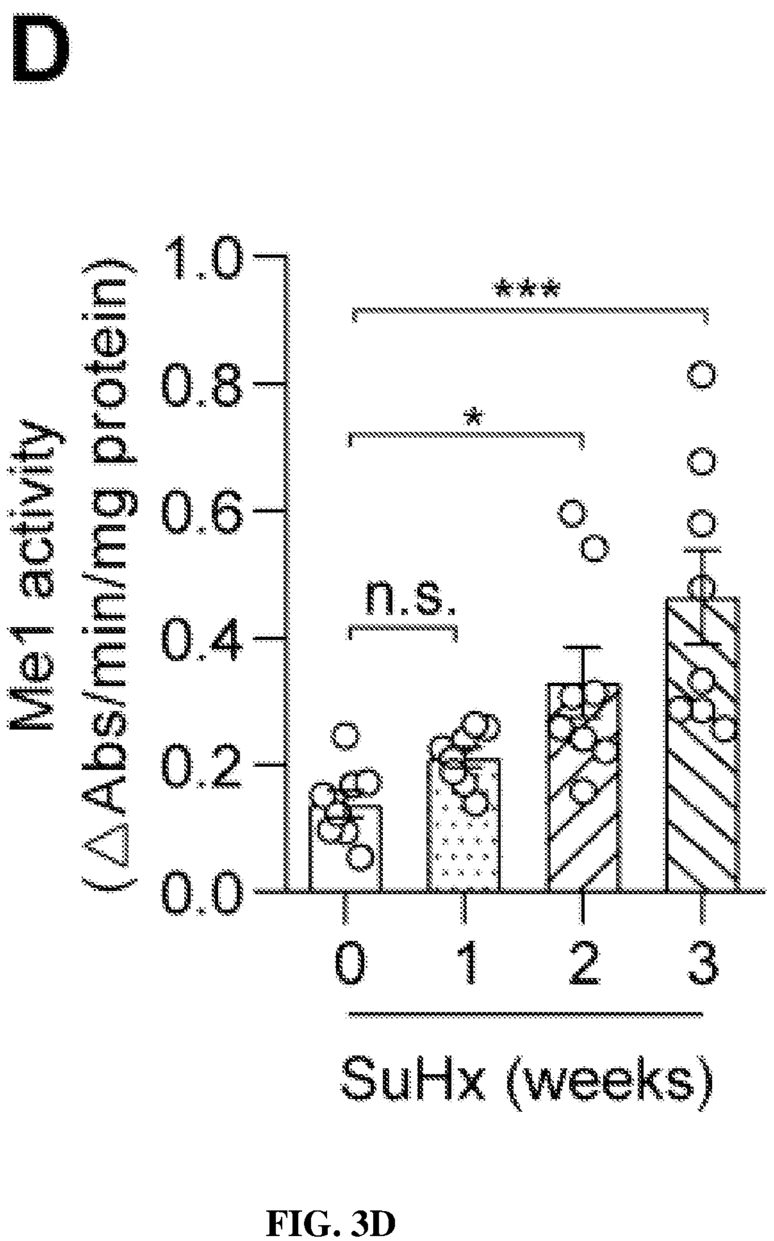

Through FIGS. 3A-D, it was found that the protein level and enzymatic activity of ME1 were significantly increased in the lung tissue of chronic hypoxia-induced and SuHx-induced PH mouse models, as shown in FIGS. 3A-D: where FIG. 3A was a representative Western blot and relative quantitative analysis of Me1 in mouse lung tissues exposed to chronic hypoxia; FIG. 3B was an enzymatic activity of the Me1 in mouse lung tissues exposed to chronic hypoxia; FIG. 3C was a representative Western blot and relative quantitative analysis of ME1 in mouse lung tissues exposed to SuHx; FIG. 3D was an enzymatic activity of the ME1 in mouse lung tissues exposed to SuHx. The above data were expressed as median±interquartile range; n=8 mice per group; a statistical method was one-way analysis of variance; *P<0.05, P<0.01, *P<0.001 and ***P<0.0001; n.s.: no significant difference.

The above experiments and results indicated that increased ME1 might be associated with the progression of PH.

Example 2

Construction and Phenotypic Evaluation of Hypoxia-Induced and SuHx-Induced PH Mouse Models of Me1+/+ and Me1−/−

2.1 Construction of Hypoxia-Induced PH Mouse Model 8 to 10 weeks old SPF-grade male Me1+/+ (wild-type mice) and Me1−/− mice (Me1 knock-out mice, a Gene ID of the Me1 gene in NCBI was 17436) weighing 25 g to 30 g) were randomly divided into a normoxia control group and a hypoxia model group. The mice in the normoxia control group were kept in an SPF-grade animal room (exposed to indoor air), and the mice in the hypoxia model group were kept in a hypoxia cabin (an oxygen concentration in the cabin was maintained at 10%). The lung tissues of all mice were collected after 4 weeks of continuous feeding, and RVSP, RVHI, and PAMT were evaluated. The specific grouping was as follows: (1) normoxia Me1+/+ group: n=8 mice; (2) normoxia Me1−/− group: n=8 mice; (3) hypoxia Me1+/+ group: n=12 mice; (4) hypoxia Me1−/− group: n=12 mice.

The Me1−/− mice were obtained according to "Li W, Kou J, Qin J, et al. NADPH levels affect cellular epigenetic state by inhibiting HDAC3-Ncor complex [J]. *Nature Metabolism,* 2021.".

An identification method of a genotype of the Me1−/− mice included:

(1) toe-cutting or tail-cutting was conducted on the mice;
(2) 50 μL of a Genotyping I solution (alkaline, NaOH) was added, and placed in a metal bath at 95° C. for 1 h;
(3) 50 μL of a Genotyping II solution (acidic, Tris-HCl) was added to terminate the reaction, then vortexed for 30 s to 60 s at 5,000 rpm, and centrifuged at 4° C. for 10 min;
(4) a PCR system was prepared, and primer sequences used for genotype identification were shown in Table 1:

TABLE 1

Primer sequences for genotype identification

| Primer | Sequence (5'-3') | SN |
|---|---|---|
| 5'loxP-F (5F) | AAGATAGGCCCAACTCAACTC GCAC | SEQ ID NO. 1 |
| 3'loxP-F (3F) | AGAAAAATCTTAATGTCAAAG TAACTG | SEQ ID NO. 2 |
| 3'loxP-R (3R) | CCCAGGTTTAAGACTGTTCAA ATTA | SEQ ID NO. 3 |

(5) preparation of a DNA gel: agarose was dissolved with 1×TAE solution to reach a final concentration of 1.5%, heated in a microwave oven P100 for about 3 min to 4 min to dissolve, air-dried until cool, a Gelstain dye (10000×) was added, a mixture was gently shaken well and introduced into a gel plate, and waited for the DNA gel to solidify; and
(6) sample loading: the sample loading hole was at a negative electrode (black), 1×TAE solution was added until just submerging the DNA gel, a sample and 10 μL of the Marker (100 bp DNA Ladder) were added;

electrophoresis: from the negative electrode (black) to a positive electrode (red), 120 V for 30 min.

2.2 Construction of SuHx-Induced PH Mouse Model 8 to 10 week-old SPF-grade Me1+/+ and Me1−/− male mice weighing 25 g to 30 g were randomly divided into SuHx model group, and the mice were kept in a hypoxia chamber (an oxygen concentration in the chamber was maintained at 10%) while receiving weekly subcutaneous injections of 20 mg/kg of SU5416 for continuous 3 weeks. The mouse lung tissues were collected and assessed for RVSP and RVHI and for PAMT. The specific grouping was as follows: (1) SuHx Me1+/+ group: n=12 mice; (2) SuHx Me1−/− group: n=12 mice.

2.3 A Method for Determining RVSP, RVHI and Evaluating PAMT of Mice was the Same as that in Example 1.

2.4 Echocardiographic Examination of Mice

Echocardiography was conducted using a Vevo 2100 ultrasound imaging platform to evaluate the dynamic changes of blood flow in the right heart of PH mice. (1) The mice were depilated to fully expose the skin on the chest wall. (2) The mice were placed on a constant-temperature heating plate at 37° C., anesthetized with 3.0% isoflurane through the nose and mouth, and the inhalation was continued with 1.5% isoflurane after the mice were anesthetized. (3) The mice were smeared with a small amount of coupling agent on their limbs and the limbs were fixed, and dynamic changes of the body temperature, heart rate, respiration rate, and electrocardiogram for mice were continuously recorded, while ensuring that the mice were in a resting state. (4) The ultrasound probe was placed, an appropriate amount of coupling agent was added, the pulmonary artery acceleration time (PAAT), pulmonary artery ejection time (PAET), and velocity-time integral were determined at a short-axis position, and then obtained frequency spectrum was saved and added with color ultrasound. (5) The above instrument was adjusted to the position of the four-chamber heart, and the position of tricuspid annulus was found along the free right ventricular wall, and TAPSE was measured. (6) Corresponding indexes were determined for statistical analysis.

2.5 Result Analysis

Figure 4:
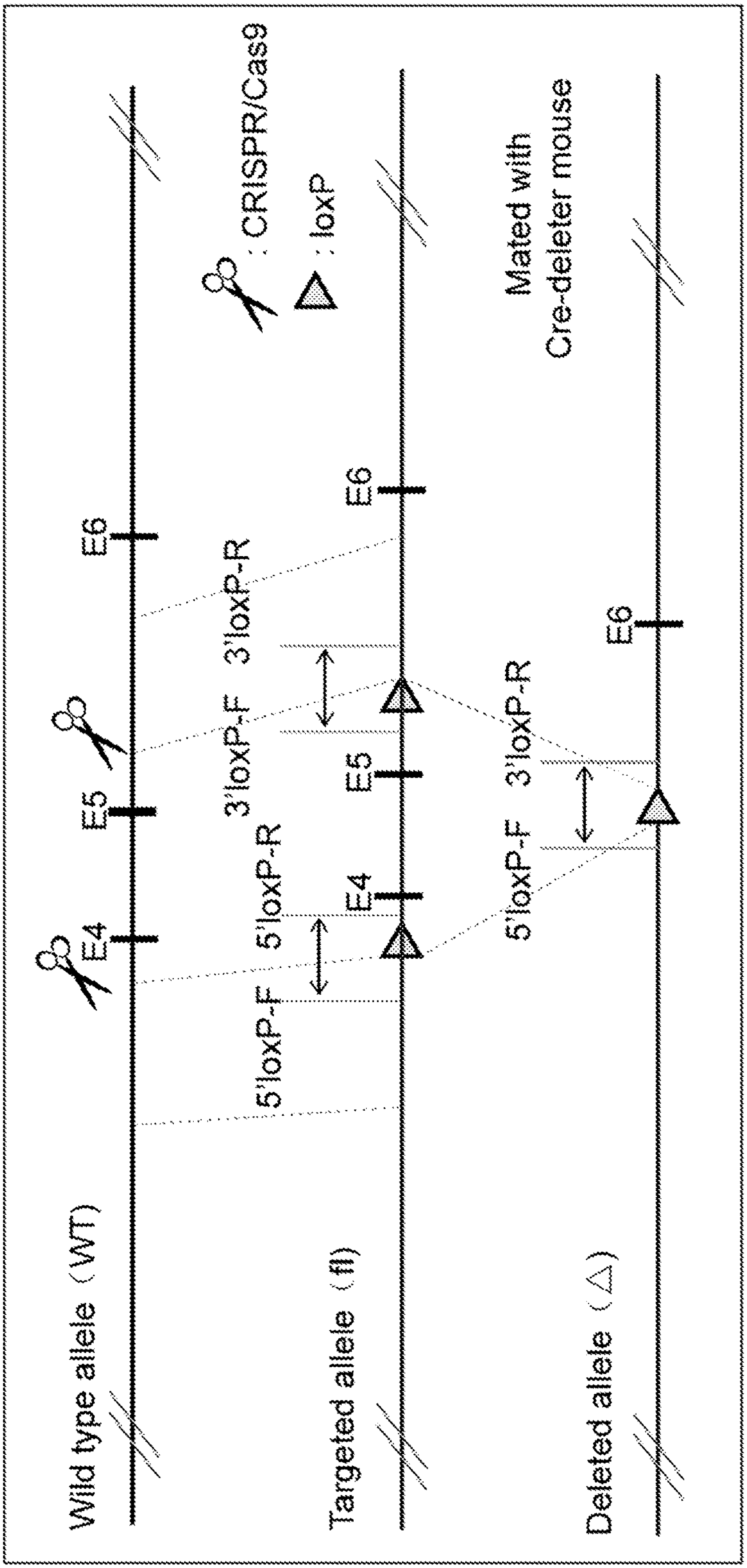
FIG. 4 shows a systemic knock-out strategy for Me1 systemic knock-out mice, where E in the figure represents exons.
Figure 5A:
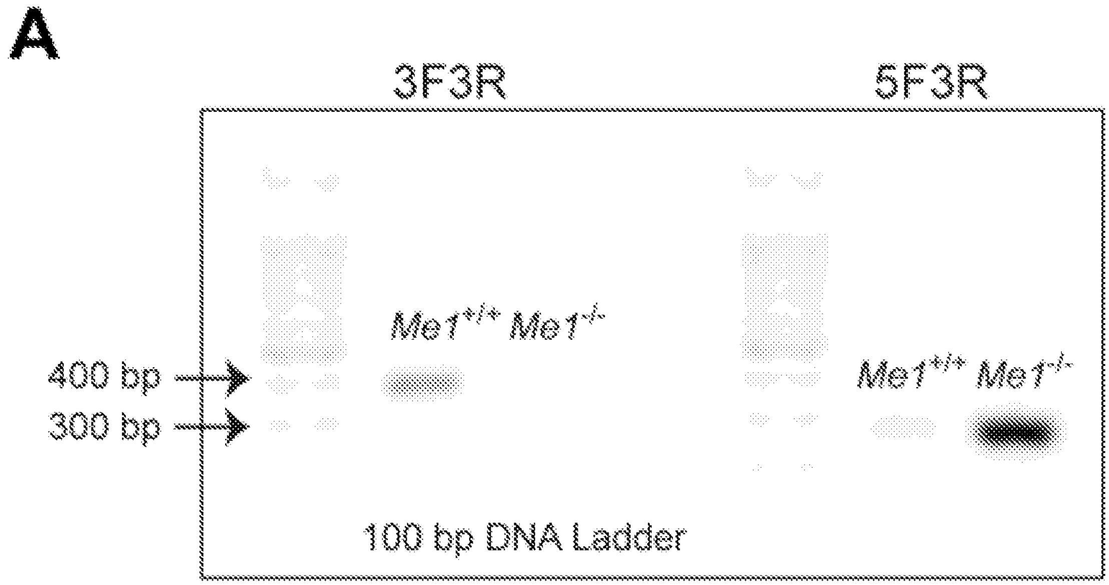
FIGS. 5A-B show successful construction of the Me1 systemic knock-out mice, where
Figure 5B:
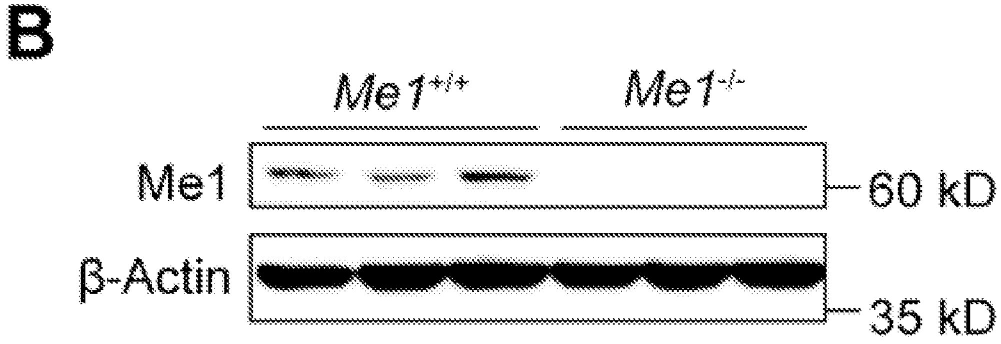

The successful construction of Me1 systemic knock-out mice was shown in FIG. 4 and FIGS. 5A-B: where FIG. 4 showed a systemic Me1 gene knock-out strategy, E in FIG. 4 represented an exon, such as E4 representing a fourth exon; FIG. 5A was a typical diagram of genotype identification of newborn wild-type (Me1+/+) and systemic knock-out (Me1−/−) mice; if 3F3R had two bands and 5F3R had one band, it meant a wild-type (Me1+/+) mouse; if 3F3R had no band and 5F3R had one band, it meant that there was a systemic gene knock-out (Me1−/−) mouse; FIG. 5B showed a representative Western blot of Me1 in the lung tissue of Me1+/+ and Me1−/− mice; as shown in FIG. 5A and FIG. 5B, it was proved that the systemic gene knock-out (Me1−/−) mice in the present disclosure were successfully constructed, and Me1 was successfully knocked out.

Figure 6A:
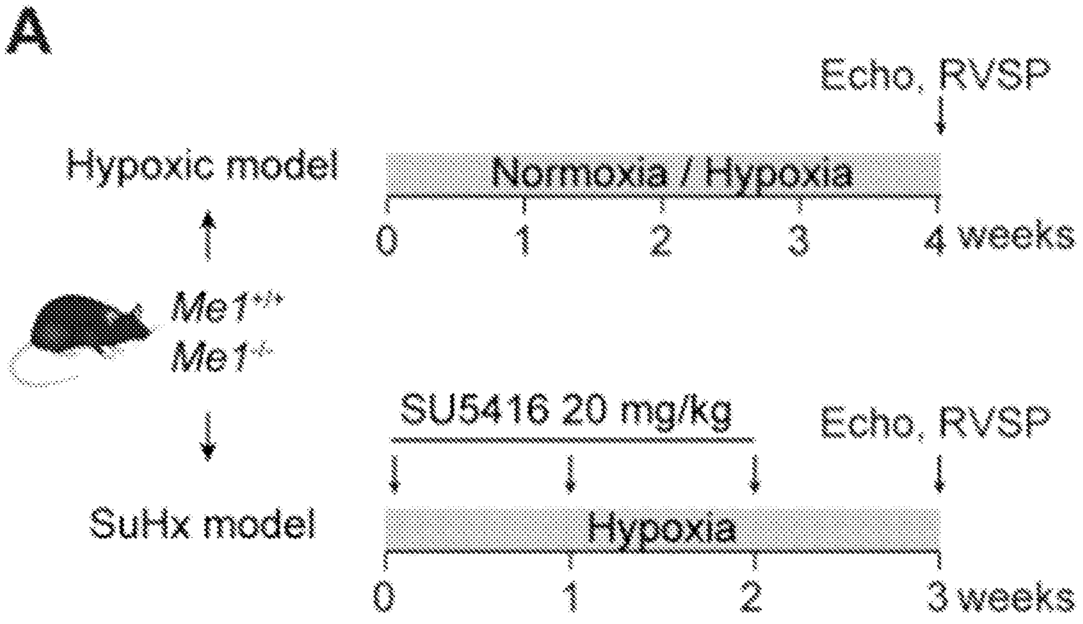
FIGS. 6A-F show that systemic knock-out of Me1 relieves chronic hypoxia- or SuHx-induced PH in mice, where
Figure 6B:
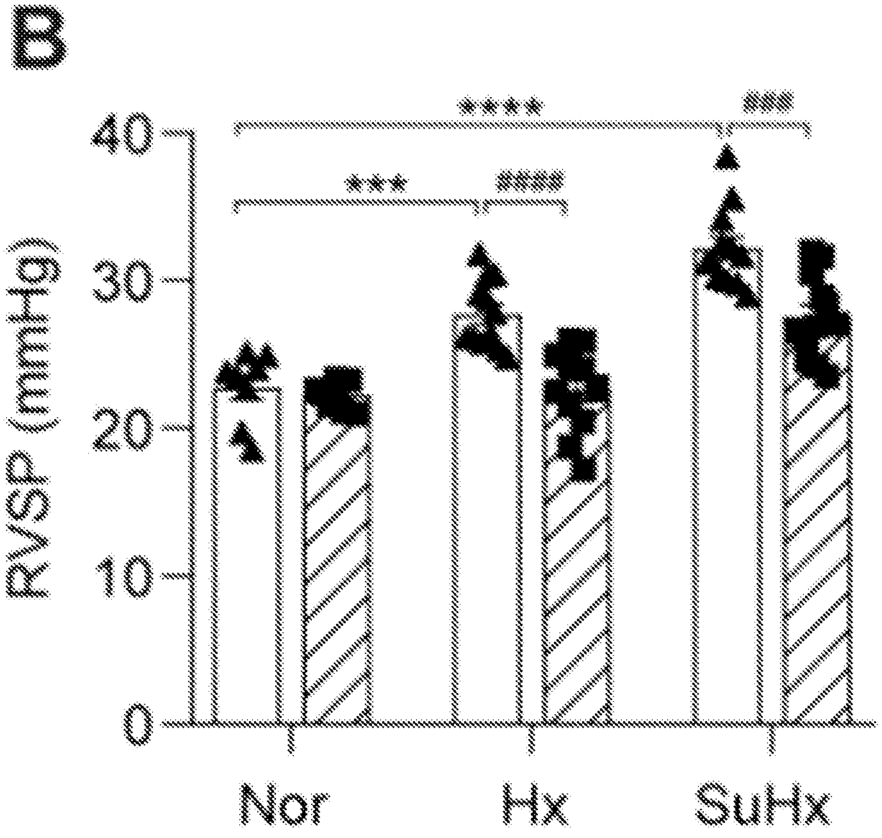
Figure 6C:
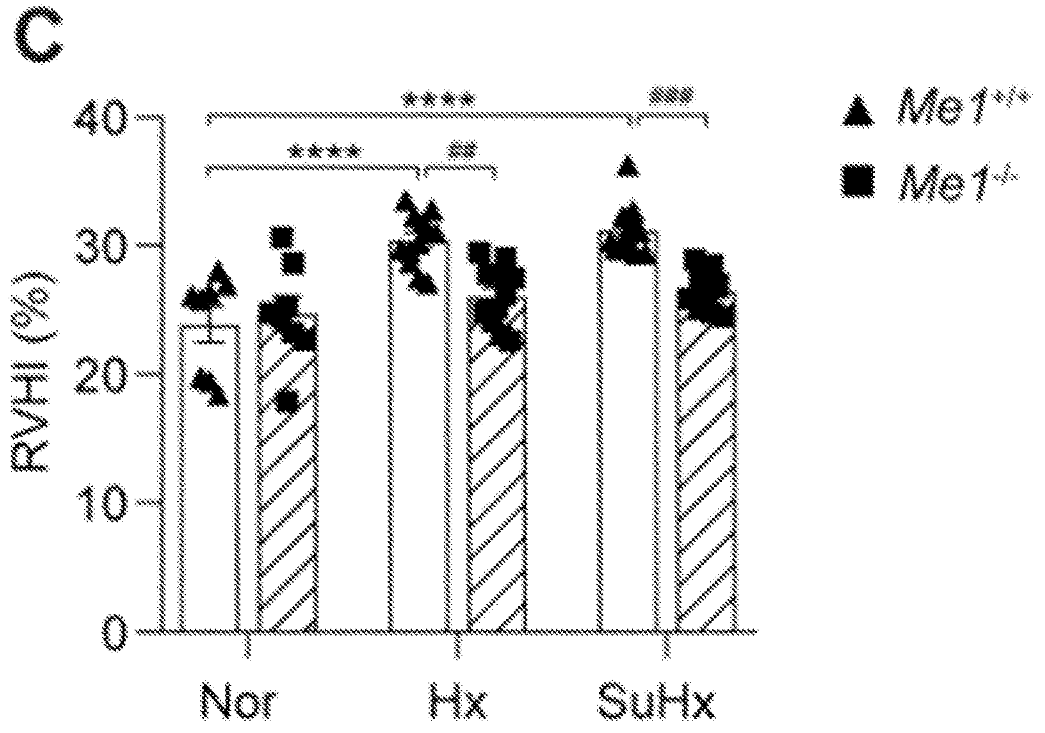

Me1+/+ and Me1−/− mice were exposed to chronic hypoxia or SuHx, and the PH mouse model was constructed as shown in FIG. 6A: it was found that compared with wild-type mice, Me1−/− mice showed a significant decrease in RVSP and RVHI, as shown in FIG. 6B and FIG. 6C. This suggested that PVR and right ventricular involvement/right heart failure in PH mice were significantly ameliorated after knock-out of the Me1 gene.

Figure 6D:
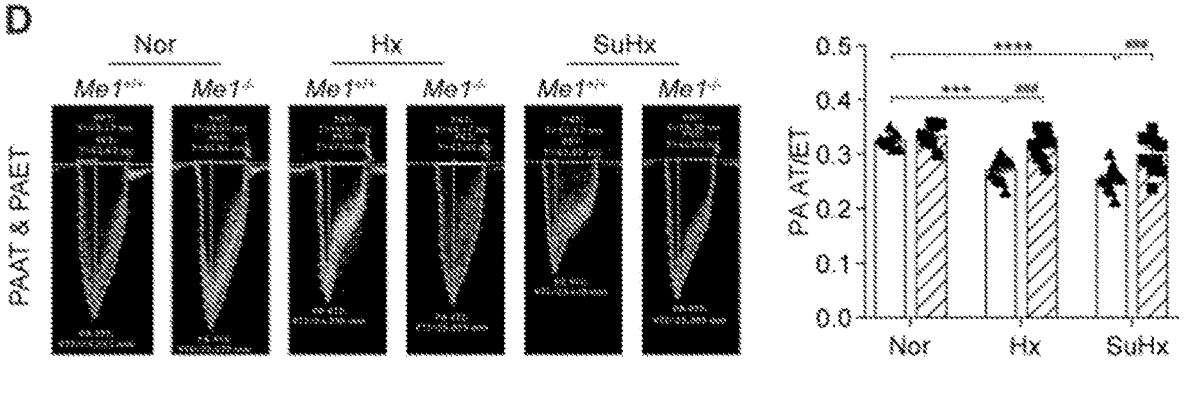
Figure 6E:
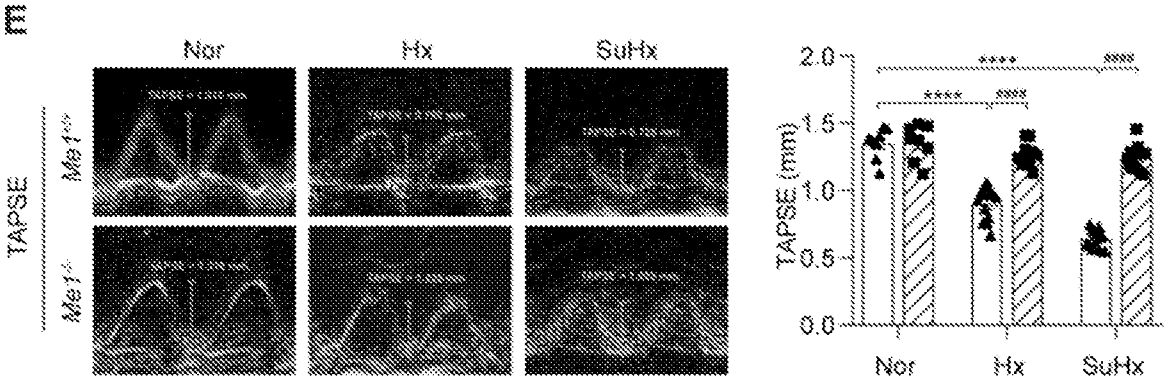

Similarly, the echocardiography of the mice suggested that after chronic hypoxia- or SuHx-induced PH, the PA AT/ET and TAPSE of Me1−/− mice were significantly higher than those of Me1+/+ mice, as shown in FIG. 6D and FIG. 6E. This indicated that the PVR and right heart systolic function of PH mice were significantly improved after knock-out of the Me1 gene.

Figure 6F:
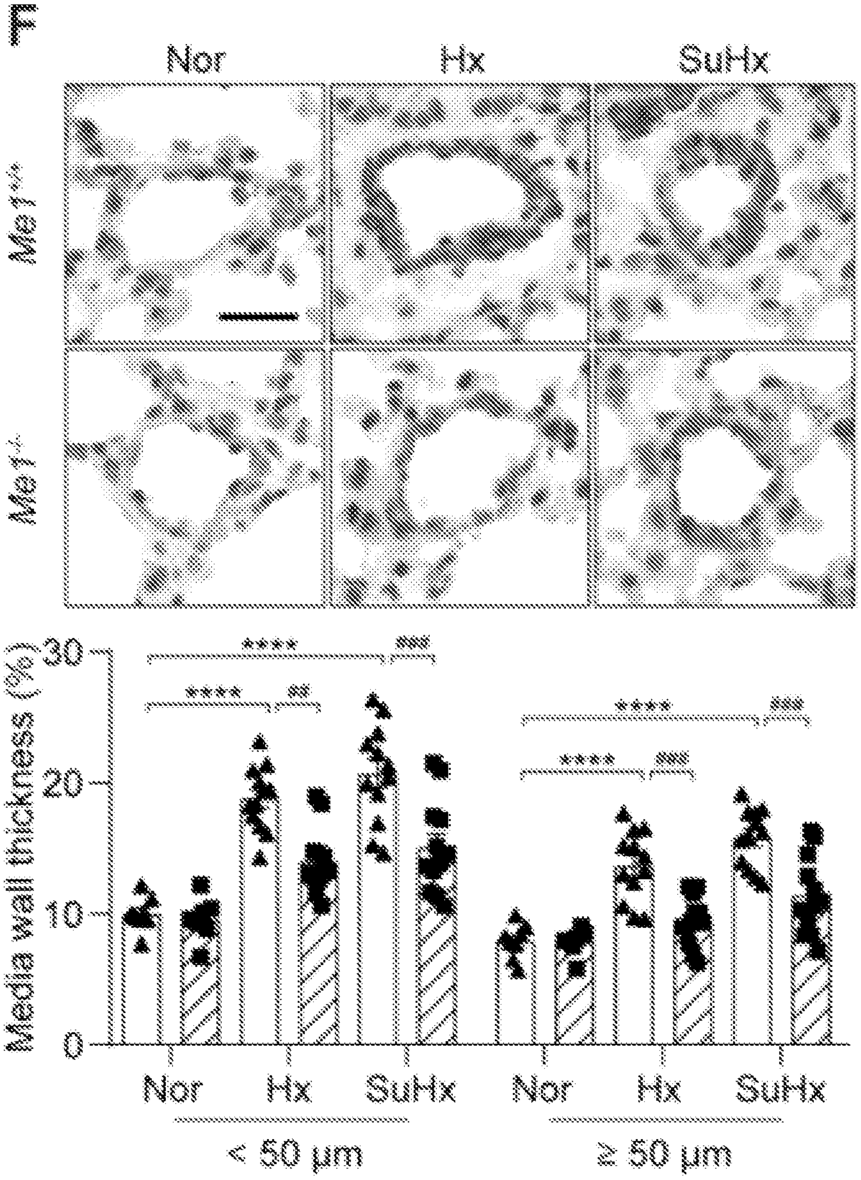

Meanwhile, the percentage of PAMT in Me1−/− mice exposed to chronic hypoxia or SuHx was significantly decreased, indicating that inhibition of Me1 improved pulmonary vascular remodeling and disease progression in PH mice, as shown in FIG. 6F. The above results in Example 2 indicated that ME1 was involved in the occurrence and development of PH, and ME1 could be used as a potential therapeutic target for PH.

Example 3

Efficacy Evaluation and Safety Evaluation of ME1 Enzymatic Activity Inhibitor (ME1*) in the Treatment of SuHx-Induced PH Mice 3.1 Dose-Finding for In Vivo Therapy of ME1*

In the present disclosure, normoxia mice are intraperitoneally injected with ME1*, at single injection doses of 1, 10, 100, 200, and 500 mg/kg, respectively, to explore the inhibitory effect of ME1* on the enzymatic activity of ME1 in mouse lung tissues.

3.2 Preventive Treatment of SuHx-Induced PH Mice with ME1*

Male SPF-grade C57BL/6J mice aged 8 to 10 weeks with a body weight of 25 g to 30 g were randomly divided into the following 4 groups:

(1) Normoxia+vehicle control group: 6 mice were fed in a normoxia environment for 3 weeks; from the second week, the mice were intraperitoneally injected with vehicle (100 mg/kg) once a day, for a total of 14 injections.

(2) Normoxia+ME1* treatment group: 6 mice were fed in a normoxia environment for 3 weeks; from the second week, the mice were intraperitoneally injected with ME1* (100 mg/kg) once a day, for a total of 14 injections.

(3) SuHx modeling+vehicle control group: 10 mice were treated with SuHx for 3 weeks (SuHx modeling method was the same as above); from the second week, the mice were intraperitoneally injected with vehicle (100 mg/kg) once a day, for a total of 14 injections.

(4) SuHx modeling+ME1* treatment group: 10 mice were treated with SuHx for 3 weeks; from the second week, the mice were intraperitoneally injected with ME1* (100 mg/kg) once a day, for a total of 14 injections.

3.3 Determination of RVSP, RVHI, and Echocardiography, and Evaluation of PAMT in Mice were the Same as Those in Example 1.

3.4 Result Analysis

Figure 7A:
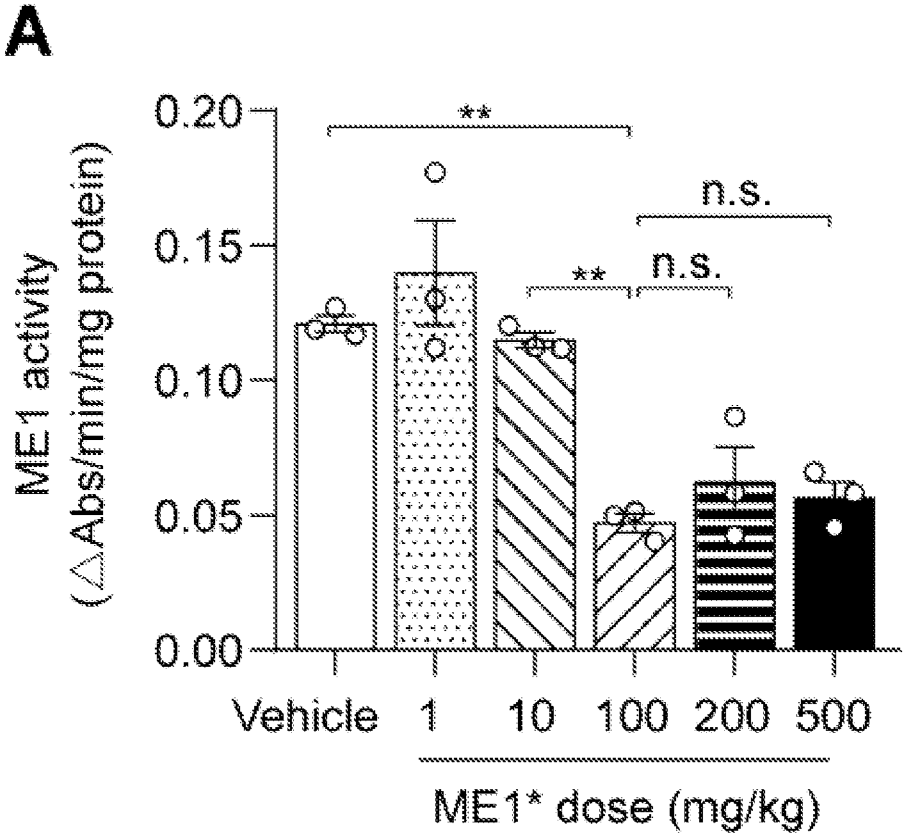
FIGS. 7A-B show preventive administration of ME1* to treat SuHx-induced PH mice, where

In the dose-finding experiment of ME1* in vivo therapy, the data in the present disclosure showed that when the dose of ME1* was greater than or equal to 100 mg/kg, the enzymatic activity of ME1 in mouse lung tissue was significantly inhibited, as shown in FIG. 7A.

Figure 7B:
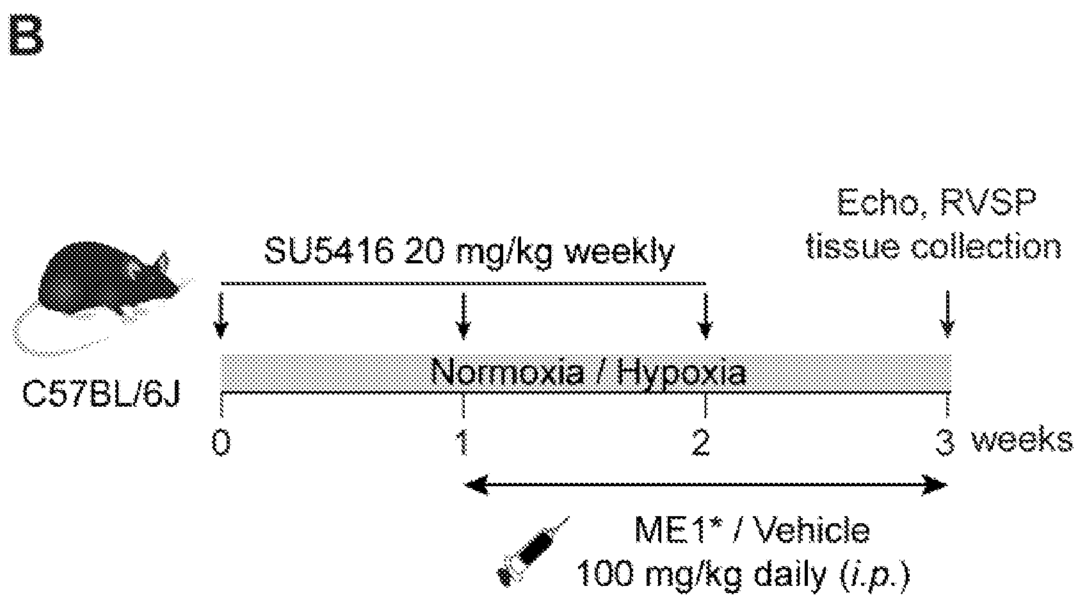

Meanwhile, considering that after SuHx stimulation for 1 week, the ME1 protein level and enzymatic activity in the mouse lung tissue were gradually increased in the present disclosure, as shown in FIG. 3C and FIG. 3D. Therefore, in the present disclosure, 100 mg/kg of ME1* or vehicle was intraperitoneally injected once a day from the second week to preventively treat SuHx-induced PH mice, as shown in FIG. 7B.

Figure 8A:
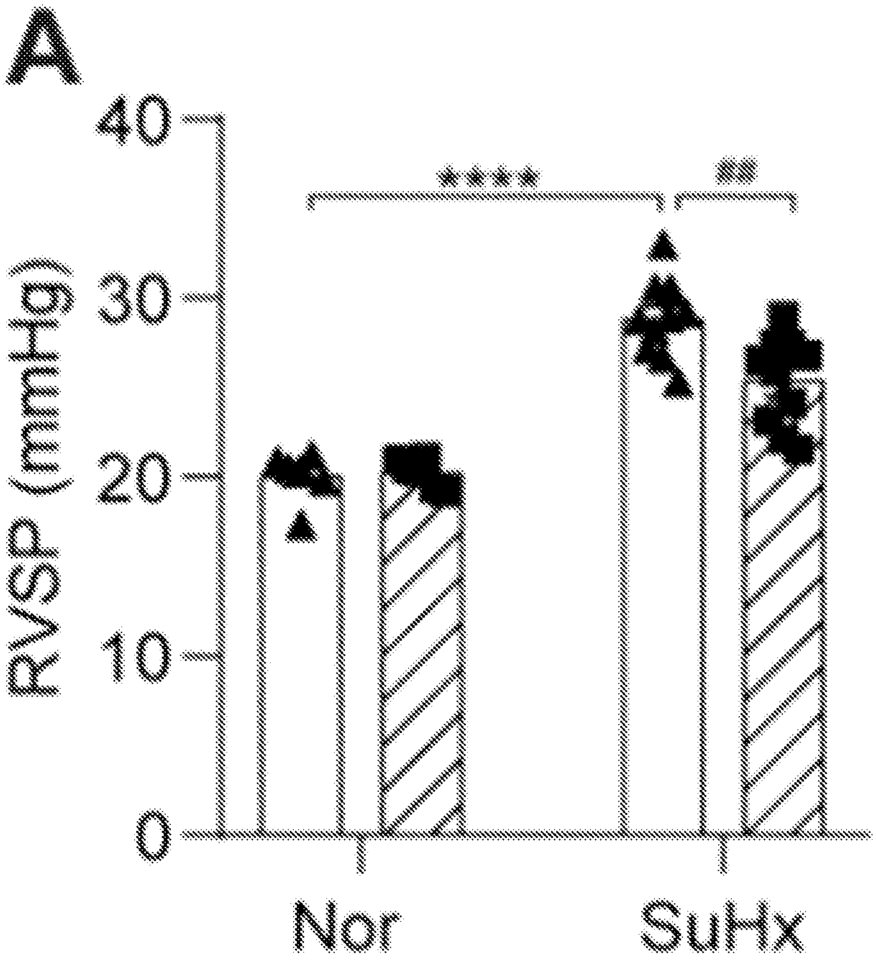
FIGS. 8A-E show curative effect evaluation of ME1* preventive treatment of SuHx-induced PH in mice, where
Figure 8B:
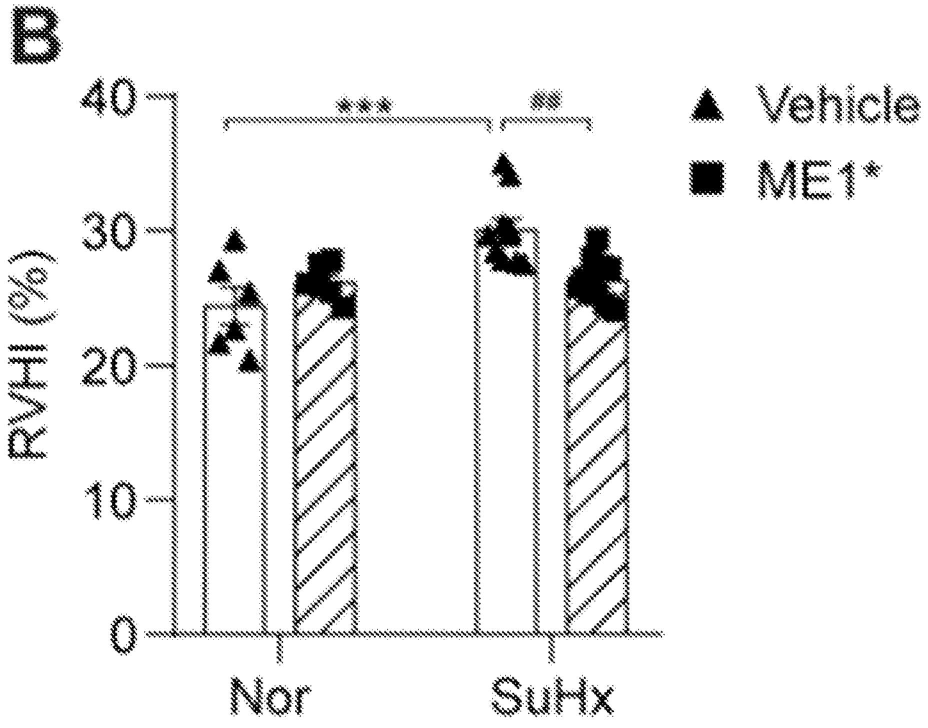
Figure 8C:
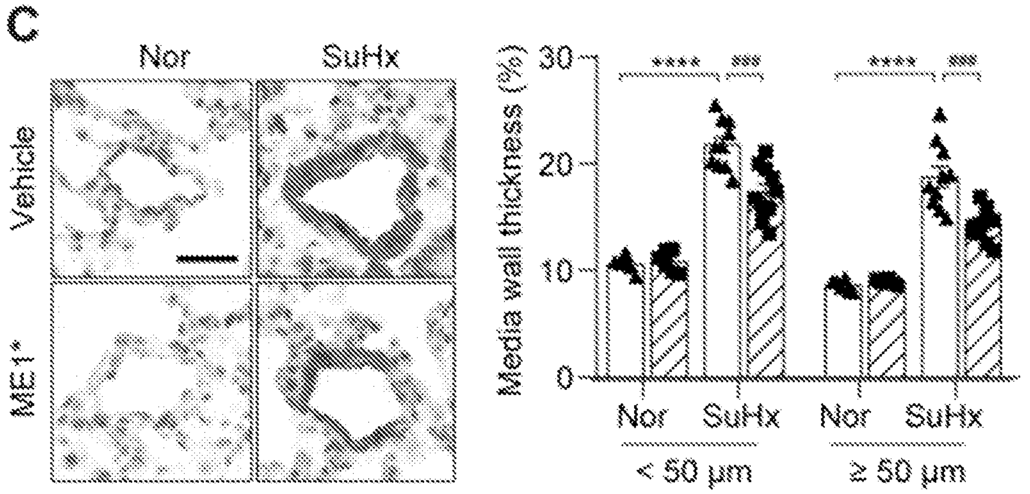
Figure 8D:
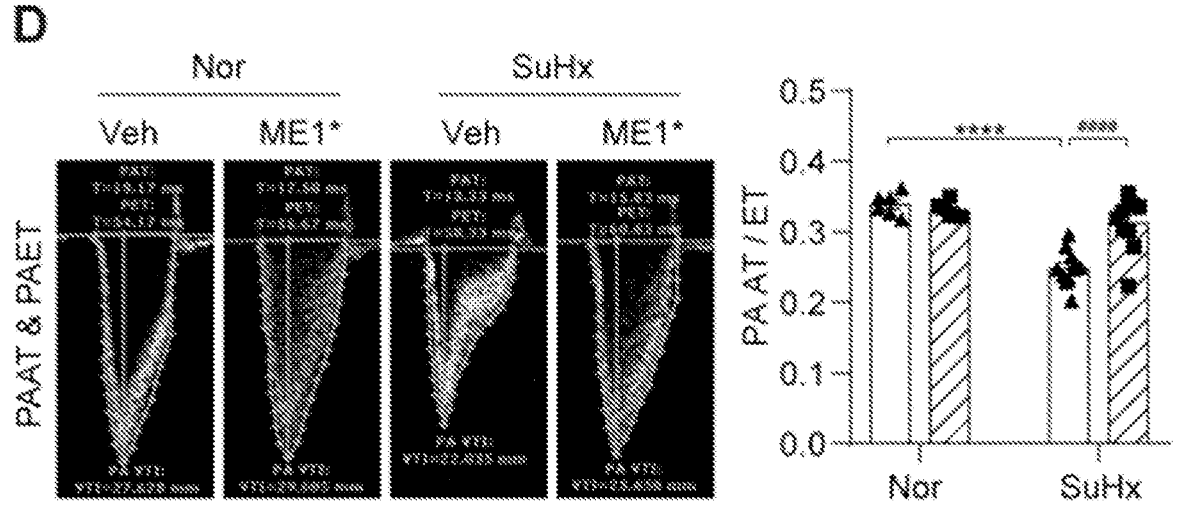
Figure 8E:
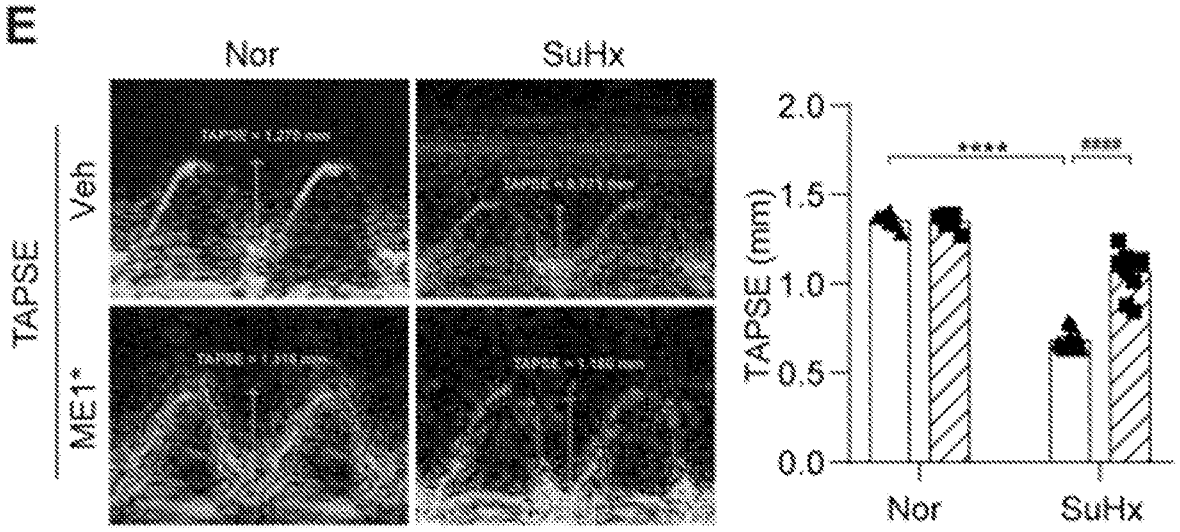

Compared with vehicle treatment, the progression of PH in ME1*-treated mice was significantly slowed, as shown by improved RVSP, RVHI (%), PA AT/ET, TAPSE, and PAMT percentage. This suggested that PVR, right heart functions, and pulmonary vascular remodeling in PH mice were significantly relieved, as shown in FIGS. 8A-E. FIG. 8A was a change of RVSP after ME1* or Vehicle preventive treatment of normoxia or SuHx mice; FIG. 8B was a change of RVHI (%) after ME1* or Vehicle preventive treatment of normoxia or SuHx mice, the RVSP and RVHI (%) of mice treated with ME1* were significantly lower than those treated with vehicle; FIG. 8C was a representative immunohistochemical image of α-SMA (red) in lung tissue sections of mice exposed to normoxia or SuHx; a change of a PAMT percentage included pulmonary artery diameters of 0 μm to 50 μm and 50 μm to 100 μm; the PAMT of mice treated with ME1* was significantly lower than that of vehicle treatment; FIG. 8D was representative echocardiogram and statistics of PA AT/ET in ME1* or Vehicle prophylactically treated normoxia or SuHx mice, the PA AT/ET of ME1*-treated mice was significantly higher than that of vehicle-treated mice; E was representative echocardiogram and statistics of TAPSE in ME1* or Vehicle prophylactically treated normoxia or SuHx mice, the TAPSE of mice treated with ME1* was significantly higher than that treated with vehicle; all data are expressed as mean±standard error; n=6 mice in normoxia group, n=10 mice in SuHx group; two-way analysis of variance; P<0.01, *P<0.001, and ****P<0.0001 (compared with normoxia-exposed Vehicle group); #P<0.05, ##P<0.01, ###P<0.001, and ####P<0.0001 (compared with SuHx-exposed ME1* group); scale bar=25 μm.

Figure 9A:
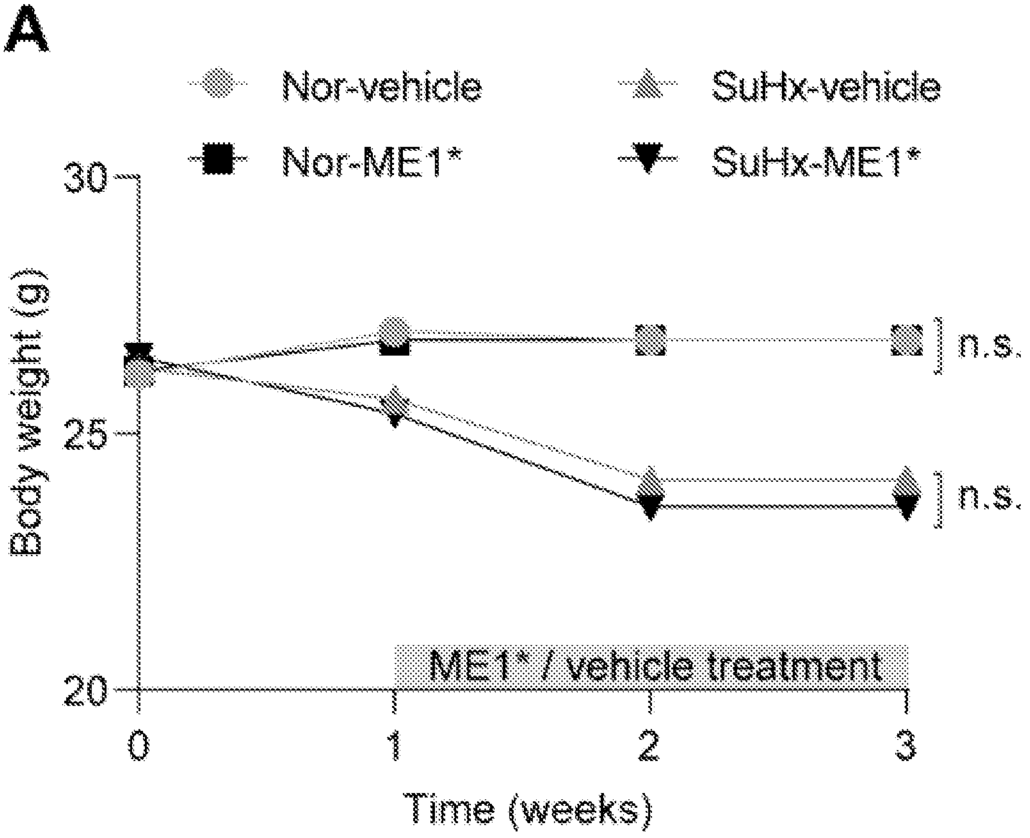
FIGS. 9A-B show safety evaluation of ME1* preventive treatment of SuHx-induced PH mice, where
Figure 9B:
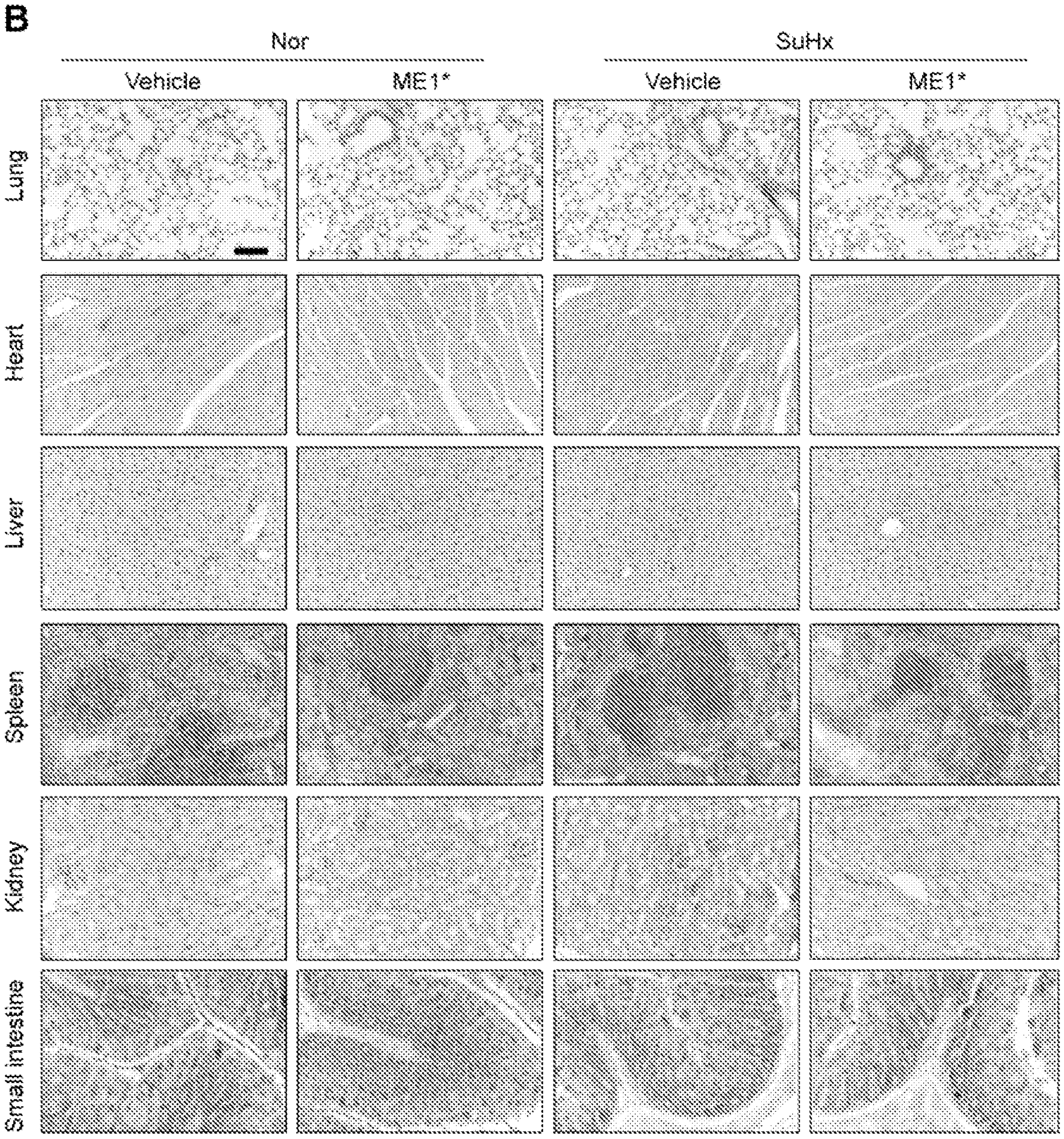

By weighing the mice every week, it was found that compared with the mice in the vehicle group, the body weight of the mice treated with ME1* was not significantly reduced, as shown in FIG. 9A. In addition, after the treatment, multiple tissues and organs of mice were collected in the present disclosure, including lung, heart, liver, spleen, kidney, and small intestine, and no obvious tissue and organ damage was found after HE staining, as shown in FIG. 9B. FIG. 9A was evaluation of an effect of ME1* on a body weight of mice after treatment; FIG. 9B was representative HE staining images of lung, heart, liver, spleen, kidney, and small intestine of the mice; the above data were expressed as mean values; n=6 mice in normoxia group and n=10 mice in SuHx group; one-way analysis of variance; scale bar=50 μm.

From the above examples, it can be seen that ME1* can safely and effectively delay SuHx-induced PH and pulmonary vascular remodeling in mice, suggesting that ME1* can be used to prepare a therapeutic drug for PH.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A method for treating pulmonary hypertension (PH), comprising: administering a malic enzyme 1 (ME1) inhibitor to a subject in need thereof; wherein the ME1 inhibitor is a small-molecule inhibitor ME1*; and the small-molecule inhibitor ME1* has a chemical structure shown in Formula I:

Formula I

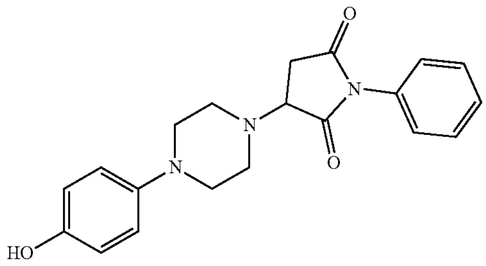

.

2. The method according to claim 1, wherein the PH is induced by hypoxia and/or SU5416/hypoxia.

3. The method according to claim 1, wherein the drug improves pulmonary vascular resistance (PVR) and/or pulmonary vascular remodeling.

4. The method according to claim 1, wherein the drug has one or more functions of reducing a right ventricular systolic pressure (RVSP), reducing a right ventricular hypertrophy index (RVHI), increasing a pulmonary artery acceleration time/ejection time (PAAT/ET), improving a tricuspid annular plane systolic excursion (TAPSE), and reducing a pulmonary artery medial thickness (PAMT).

* * * * *